United States Patent [19]
Deharde et al.

[11] Patent Number: 5,658,241
[45] Date of Patent: Aug. 19, 1997

[54] MULTI-FUNCTIONAL DYNAMIC SPLINT

[75] Inventors: Mark Deharde, Phoenixville; Kenneth Patchel, Kennett Square, both of Pa.

[73] Assignee: Ultraflex Systems, Inc., Malvern, Pa.

[21] Appl. No.: 443,200

[22] Filed: May 17, 1995

Related U.S. Application Data

[63] Continuation of Ser. No. 210,763, Mar. 22, 1994, abandoned, which is a continuation-in-part of Ser. No. 740,387, Aug. 5, 1991, Pat. No. 5,358,469, which is a continuation-in-part of Ser. No. 477,460, Feb. 9, 1990, Pat. No. 5,036,837.

[51] Int. Cl.⁶ .................................................... A61F 5/00
[52] U.S. Cl. ............................ 602/5; 602/23; 602/26
[58] Field of Search .................................. 128/869, 882; 602/5, 23, 26, 27

[56] References Cited

U.S. PATENT DOCUMENTS

| | | |
|---|---|---|
| 1,847,823 | 1/1932 | Dresser . |
| 2,067,567 | 1/1937 | Gruca . |
| 2,832,334 | 4/1958 | Whitelaw . |
| 3,707,963 | 1/1973 | Keropian . |
| 3,826,251 | 7/1974 | Ross . |
| 4,252,111 | 2/1981 | Chao . |
| 4,340,041 | 7/1982 | Frank . |
| 4,397,308 | 8/1983 | Hepburn . |
| 4,485,808 | 12/1984 | Hepburn . |
| 4,489,718 | 12/1984 | Martin . |
| 4,493,316 | 1/1985 | Reed . |
| 4,508,111 | 4/1985 | Hepburn . |
| 4,538,600 | 9/1985 | Hepburn . |
| 4,614,181 | 9/1986 | Karlsson . |
| 4,633,867 | 1/1987 | Kausek . |
| 4,657,000 | 4/1987 | Hepburn . |
| 4,697,583 | 10/1987 | Mason et al. . |
| 4,726,361 | 2/1988 | Farley . |
| 4,738,252 | 4/1988 | Friddle . |
| 4,771,768 | 9/1988 | Crispin . |
| 4,817,588 | 4/1989 | Bledsoe . |
| 4,844,057 | 7/1989 | Hoy . |
| 4,846,842 | 7/1989 | Connolly ............................. 602/26 |
| 4,865,024 | 9/1989 | Hensley ............................. 602/26 |
| 4,938,206 | 7/1990 | Harris ............................... 602/26 |
| 4,961,416 | 10/1990 | Moore ............................... 602/26 |
| 4,982,732 | 1/1991 | Morris . |
| 5,000,169 | 3/1991 | Swicegood et al. . |
| 5,002,044 | 3/1991 | Carter . |
| 5,013,037 | 5/1991 | Stermer . |
| 5,025,801 | 6/1991 | Callaway . |
| 5,036,837 | 8/1991 | Mitchell ............................. 602/26 |
| 5,092,321 | 3/1992 | Spademan . |
| 5,103,807 | 4/1992 | Makaran . |
| 5,117,814 | 6/1992 | Luttrell .............................. 602/26 |

*Primary Examiner*—Michael A. Brown
*Attorney, Agent, or Firm*—Sixbey, Friedman, Leedom & Ferguson

[57] ABSTRACT

A dynamic splint has a bi-directional torsional power unit fastened between first and second struts to selectively deliver force opposing either extension or flexion. The power unit is mounted about a hinge pin and can be rotated between two positions. In the first position, the power unit is locked relative to the first strut and the torsion spring opposes relative movement of the second strut in a first direction. In the second position, the power unit is locked relative to the second strut. In this second position, the torsion spring opposes movement of the first strut relative to the second strut, providing torsion in an opposite direction from that of the first position. Self-aligning contour plates on the struts conform to the anatomy and provide a mechanical interlock to bony prominences on the patient's limbs. A universal integral soft cuff/strap design simplifies set-up and provides infinite adjustment capability for increased comfort and performance. Infinitely adjustable telescoping struts facilitate custom fitting adjustment. A cam locking mechanism selectively disables the torsional force of the power unit and locks the splint in a desired position.

34 Claims, 19 Drawing Sheets

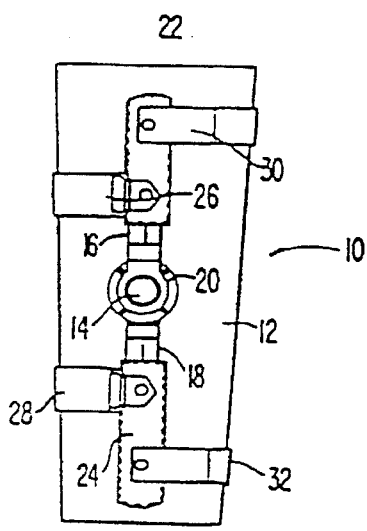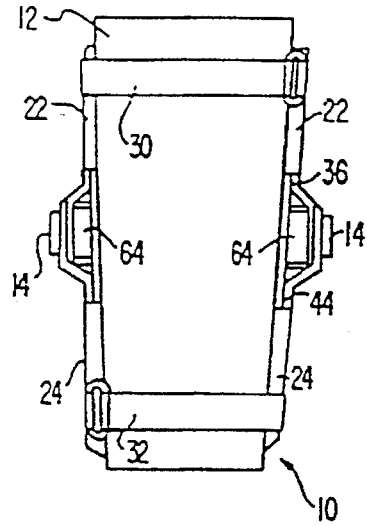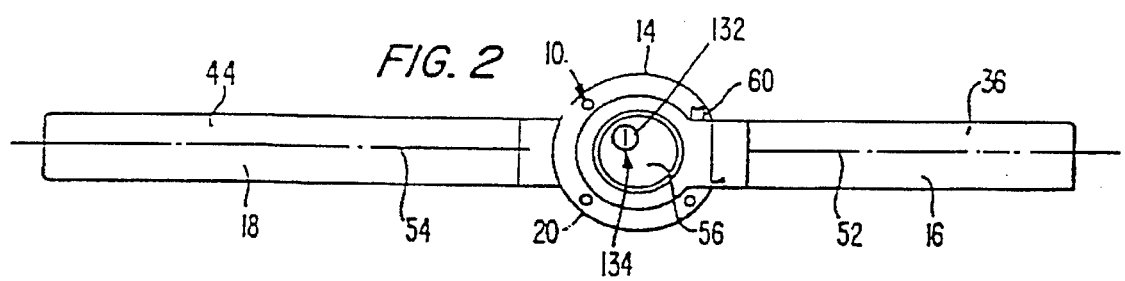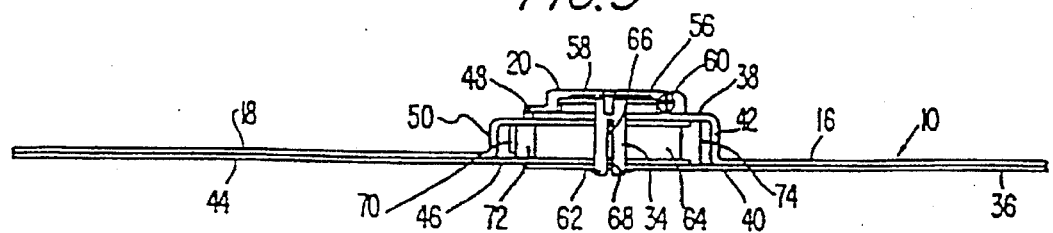

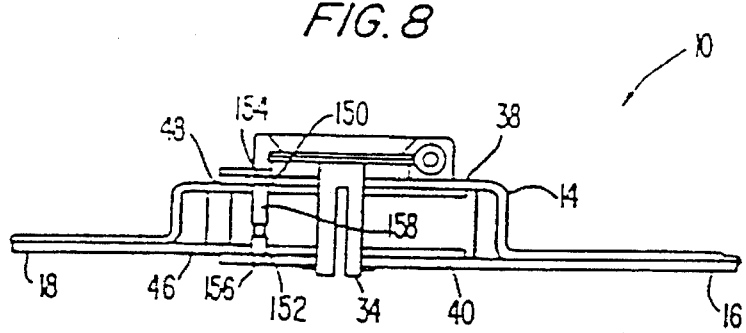
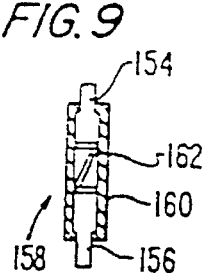
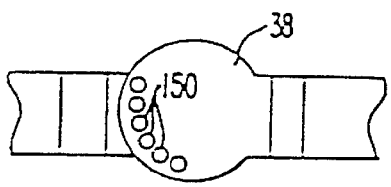
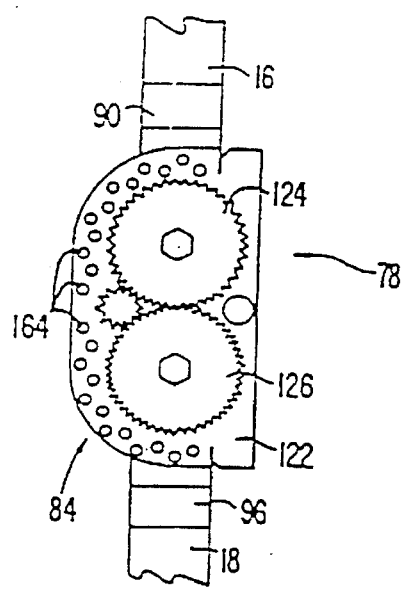
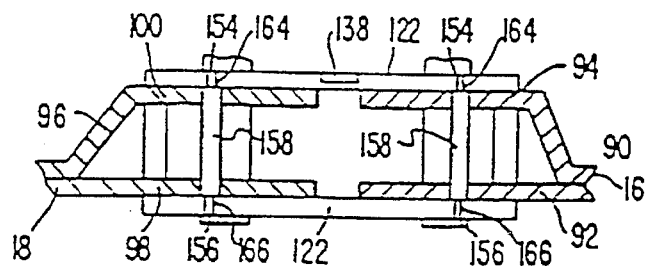

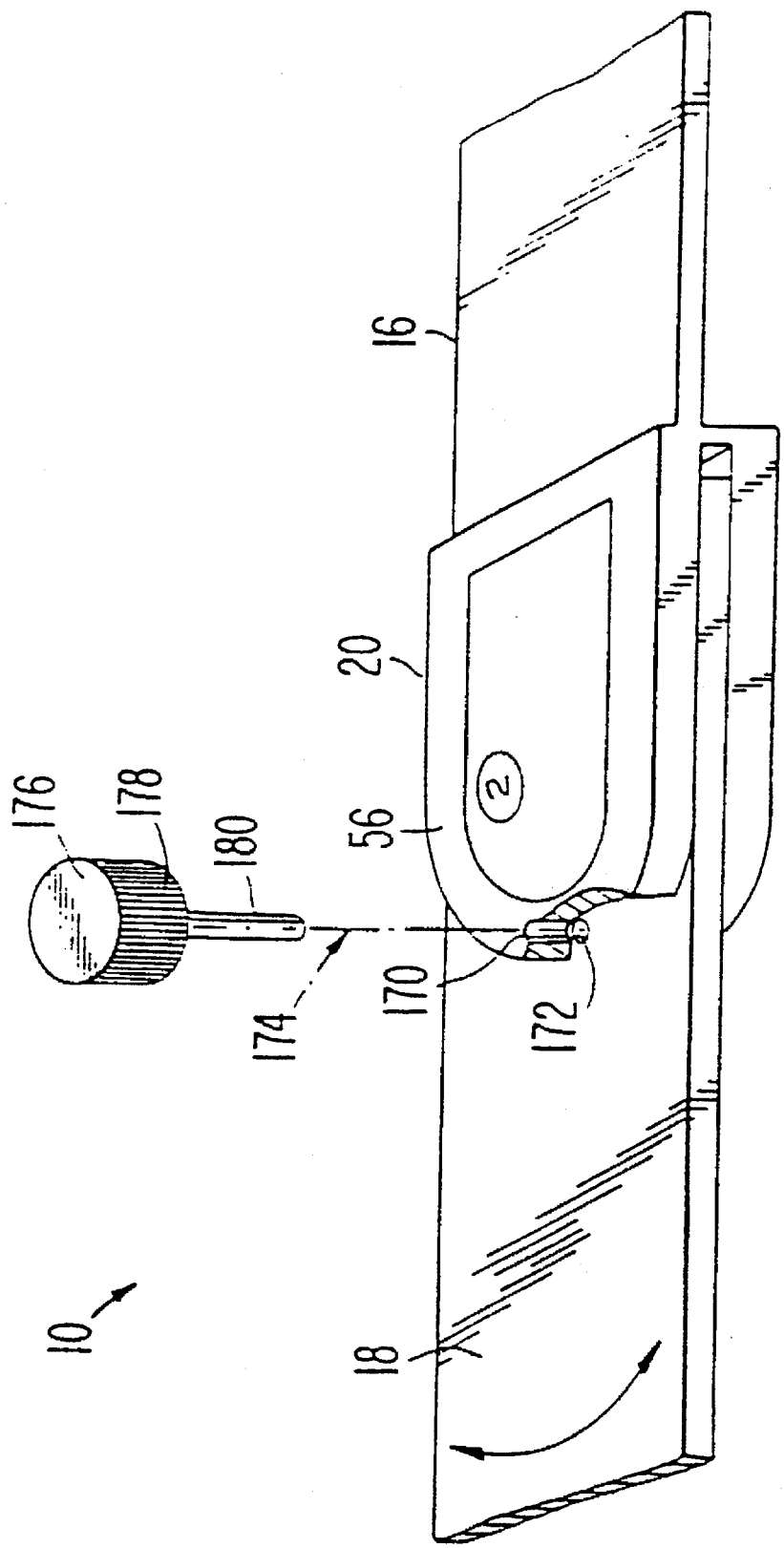

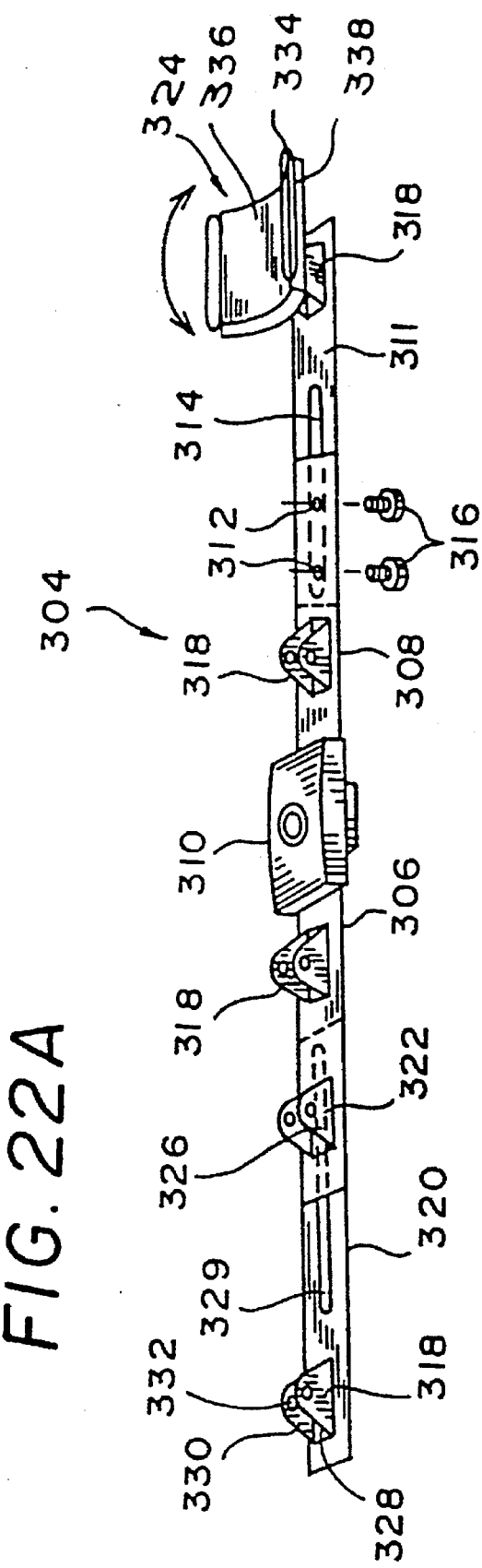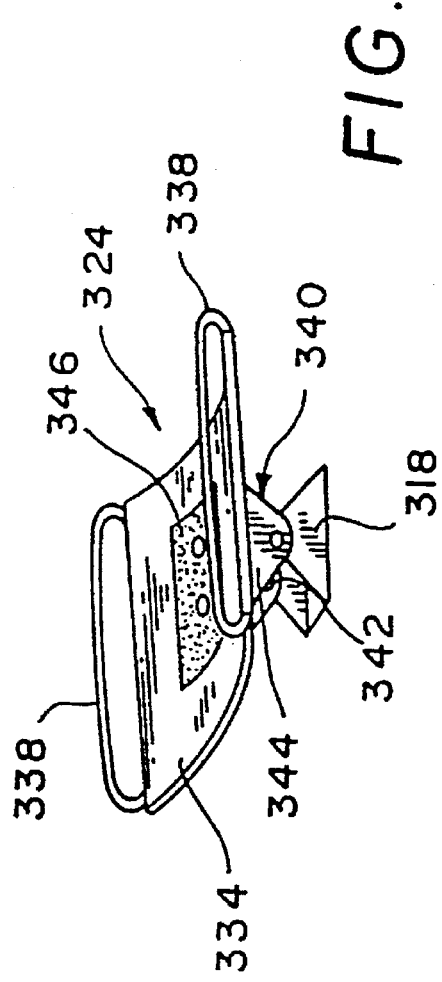
FIG. 22A
FIG. 22B

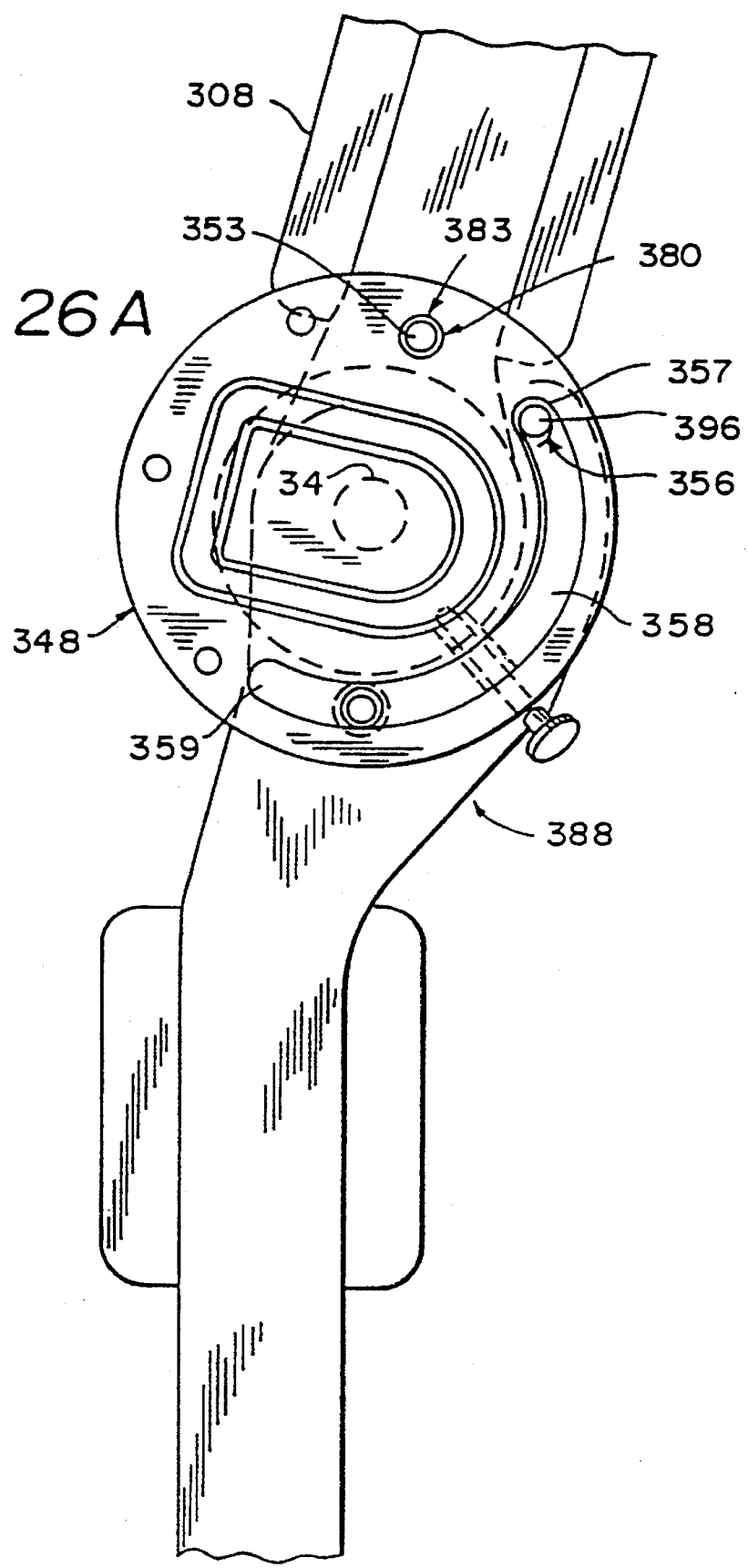

MULTI-FUNCTIONAL DYNAMIC SPLINT

This application a continuation of Ser. No. 08/210,763 filed Mar. 22, 1994 now abandoned, which is a continuation-in-part of U.S. patent application Ser. No. 07/740,387 filed Aug. 5, 1991, now U.S. Pat. No. 5,358,469, which is a continuation-in-part of Ser. No. 07/477,460 filed Feb. 9, 1990, now U.S. Pat. No. 5,036,837.

FIELD OF THE INVENTION

The present invention relates to splint assemblies generally, and more particularly to a dynamic splint adapted to exert an adjustable force or tension at a body joint.

BACKGROUND OF THE INVENTION

In recent years, dramatic advances have been made in the development of lightweight, compact mechanisms for correcting common and debilitating injuries to body joints such as fingers, wrists, knees, elbows and the like. Perhaps the greatest advances have been made in the design of orthotic brace units which counteract instabilities in a joint by reinforcing the joint as a whole to prevent unwanted motion. Such orthotic devices are typically formed with a mechanical joint supported by a pair of bracing members. The mechanical joint is defined by a pair of side bars, each of which has a hinge-like pivoting joint in its middle with the top and bottom ends of the side bars being connected to bracing members which fit around a body portion above and below the joint to be supported. These devices operate generally by confining the movement of the joint as it bends so that unwanted motions are eliminated or at least minimized. The most commonly known orthoses are orthotic knee braces of the type commonly used by athletes who have suffered injuries to either the ligaments that interconnect the lower femur and upper tibia, or to the bones themselves, which result in knee instabilities.

Joint instability is not the only debilitating condition of a body joint which requires correction. The operation of a body joint may be impaired in a manner which inhibits the operation of the joint in accomplishing extension or flexion. For example, a flexion contracture prevents full extension of the joint, while an extension contracture prevents the joint from being bent or flexed to the full extent. Obviously, the treatment of a flexion contracture or an extension contracture requires more than the mere support against instability provided by many conventional orthotic devices.

To treat flexion and extension contractures, spring-biased splint units have been developed to provide a force across a body joint. These splint devices provide tension which operates in opposition to a flexion or extension contracture and thereby not only provide support in instances where muscular weakness exists, but also enhance rehabilitation. One type of known adjustable spring-loaded splint includes a pair of lower struts and a pair of upper struts of tubular configuration which are pivotally interconnected. Spring biasing units mounted within the tubular struts are adapted to apply an adjustable force at the pivot point which tends to align the two pivoted struts. Such an adjustable splint mechanism is illustrated by U.S. Pat. Nos. 4,397,308; 4,485,808; 4,508,111; 4,538,600 and 4,657,000 to George R. Hepburn.

Although known adjustable splints operate effectively to apply tension across a joint, they are relatively heavy and bulky and consequently impede to some extent free activity at the affected joint. The heavy tubular strut assemblies used in prior art splints are generally not coextensive from the connecting pivot point, and thus may be brought into only parallel rather than axially aligned relationship. It is impossible to contour these heavy struts to conform to the limb of a user, and the degree of pivotal movement within which the applied force is linear is generally small. Such splints generally use straight line springing against a cam. The rotational force applied by the cam is extremely non-linear due to the changing moment arm on the cam surface. This variation prevents the application of a constant therapeutic force and requires constant adjustment to the spring force through the desired range of motion.

Finally, with known prior art adjustable splints, the bias adjustment mechanism for the splint is difficult to reach, and the degree of adjustment is often difficult to ascertain. Accurate adjustment of the bias for such prior art units with the splint in place is not easily accomplished, and the bias structure employed does not facilitate polycentric joint structures of the type better suited to the motion of certain joints, such as the knee.

In general, prior art splints have been constructed for force application in either a flexion or contraction direction, but not both. However, U.S. Pat. No. 4,370,977 to Mauldin shows a knee brace with a spring connected to a hinge member which may be used to resist motion in either direction. Resistance in one direction is transformed to resistance in the opposite direction by removing a thumbscrew and the torsion spring, and reinstalling the torsion spring in different holes on the hinge portion. However, mechanisms of this type do not provide an even adjustment of force capability, and reversing the direction of force application requires complexity in the operations required to reverse the device.

U.S. Pat. No. 5,052,379 to Airy et at. shows a brace with frame sections connected by a pivot joint which resists relative movement of the frame sections in either or both directions about the pivot axis. A removably connected torsion spring provides the resistive force. This reference, however, uses different torsion springs to impose the resistance desired, rather than changing the position of a single torsion spring.

SUMMARY OF THE INVENTION

It is a primary object of the present invention to provide a novel and improved dynamic extension or flexion splint for the treatment of joint contractures which is easily applied to a body member in the area of the joint to be treated and which is both compact and lightweight.

Another primary object of the present invention is to provide a mechanism for applying an accurate adjustable force with near-constant linearity opposing movement of a body joint, consistent reset-ability and easy read-ability.

Another object of the present invention is to provide a novel and improved dynamic extension or flexion splint having opposed strut assemblies which incorporate flat strut members adapted to be contoured in place to conform to a body member. This permits customizing the fit of the splint for greater comfort.

A further object of the present invention is to provide a novel and improved dynamic extension and/or flexion splint having opposed strut assemblies which may be easily removed from a strut assembly support unit. Each strut assembly includes two elongated strut members which slide into pockets on either side of the joint to be treated.

Yet another object of the present invention is to provide a novel and improved dynamic extension and/or flexion splint which provides a full range of motion for a joint under treatment. The splint incorporates strut members which pivot at a mechanical joint through the maximum anatomical range plus 10° hyperextension. Tension is applied to the strut members by a torsion or power-spring type of biasing unit with near linear force characteristics mounted at the mechanical joint, and the spring tension is adjustable by means of a bias adjustment mechanism which is also located at the mechanical joint. Thus, the tension applying spring and the bias adjustment are both located entirely at the mechanical joint for the splint.

A further object of the present invention is to provide a novel and improved dynamic extension and/or flexion splint having a polycentric joint mechanism which is adapted to provide greater than the full anatomical range of motion. Elongated strut members are mounted on the joint for pivotal motion about two spaced parallel pivot axes. Each strut member is biased by a separate spring, and the bias of plural springs is simultaneously adjusted by a bias adjustment mechanism. An indicator at the mechanical joint provides an indication of the degree of bias which is set into the springs.

A still further object of the present invention is to provide a dynamic extension and/or flexion splint having an adjustable spring mechanism which is reversible to provide either flexion or extension resistance.

Another object of the present invention is to provide an adjustable-bias dynamic extension and/or flexion splint with a visible indicator showing the relative magnitude of the bias force applied.

A further object of the present invention is to provide an adjustable-bias dynamic extension and/or flexion splint wherein the bias force is produced by a mechanism in a housing located at the joint, and a visible indicator of the relative magnitude of the bias force is provided when different inscribed portions of a member rotating upon bias force adjustment become visible through an aperture as a result of the rotation.

It is also an object of the present invention to provide a dynamic extension and/or flexion splint, having portions attachable to a human body on each side of a body joint and applying a bias force to the joint, which also has a mechanism for selectively negating the bias force during attachment or removal of the splint.

Another object of the present invention to provide a dynamic extension and/or flexion splint, having portions attachable to a human body on each side of a body joint and applying a bias force of adjustable magnitude to the joint, which also has a mechanism for selectively negating the bias force during attachment or removal of the splint without changing the magnitude adjustment setting the bias force to be applied.

It is also an object of the present invention to provide a dynamic splint which is designed to be easily attached to a body joint in a flexible manner that compensates for deviations in the geometry of the joint and permits attachment of the splint even to damaged or swollen joints.

Another object of the present invention is to provide a dynamic splint with pivotable self-aligning pads that compensate for swelling and variations in patient bone and tissue structure.

It is also an object of the present invention to provide a dynamic splint with pivotable self-aligning pads located to rest against bony prominences such as joint condyles and thereby prevent migration of the splint along the limb during ambulation.

A further object of the present invention is to provide a dynamic ankle splint with a dynamic cradle for applying an adjustable torsional load to the ball of the foot to correct inversion and eversion of the ankle.

Yet another object of the present invention is to provide a dynamic wrist splint which is attached to the forearm, and applies a bias force to the hand through a novel palm interface.

It is also an object of the present invention to provide a dynamic wrist splint which distributes forces over a large area of the palm.

A further object of the present invention is to provide a dynamic wrist splint which adjusts over the wrist's arc of rotation to comfortably distribute forces over the palm.

Another important object of the invention is to provide a dynamic splint having a bi-directional power unit that can be readily switched between flexion and extension force modes.

It is also an object of the invention to provide a reversible power unit with a spring fastened between first and second struts to selectively deliver force opposing either extension or flexion.

Another object of the invention is to provide a reversible bi-direction power unit which is mounted about a hinge pin and can be selectively rotated between two positions to apply force in one of two directions. In the first position, the power unit is locked relative to a first strut and a spring in the power unit opposes relative movement of a second strut in a first direction. In the second position, the power unit is locked relative to the second strut, and the spring opposes movement of the first strut relative to the second strut, applying force in the opposite direction from the force provided in the first position.

Another object of the present invention is to provide a novel universally sized soft cuff/strap design for a dynamic splint that simplifies set-up and provides infinite adjustment capability for increased comfort and performance. Infinitely adjustable telescoping struts are also provided to facilitate custom fitting adjustment.

Another object of the invention is to provide an improved cam locking mechanism for selectively disabling the torsional force of the power unit when donning or doffing the splint.

These, and other objects of the present invention are accomplished by providing an adjustable splint having a pair of elongated strut assemblies which each incorporate a pivotal joint between the ends thereof. These strut assemblies are supported on opposite sides of a body joint by a strut support unit which is mountable on a body member and which locates the pivotal joint in alignment with a body joint. Each strut assembly includes a first elongated strut member and a second elongated strut member which extend from the pivotal joint. The elongated strut members of each strut assembly are flat units which may be contoured to match the contour of the body member upon which the splint is mounted. The pivotal joint operates to connect one end of the first and second strut members for pivotal movement about a pivot axis between a first extended position where the elongated strut members extend outwardly from opposite sides of the pivotal joint and a second closed position where the first and second strut members extend outwardly in close proximity from the same side of the pivotal joint. A bias unit is provided at the pivotal joint to oppose pivotal movement of the strut members in a first direction and to aid such pivotal movement in a second opposite direction. The magnitude of the bias is adjustable by a mechanism which is also located at the pivotal joint, while the range of motion provided by the joint can be altered by spring loaded pins which operate as stops for the strut members. The relative magnitude of bias provided is indicated in a preferred embodiment by numeric markings on a rotating member of the adjustment mechanism. The portion of the rotating member having the appropriate magnitude marking is visible through an aperture in the housing. A pin lock mechanism is provided for locking the strut members to prevent relative movement thereof and to temporarily prevent the application of force by the bias unit during attachment and removal of the splint.

Specific preferred embodiments of the invention include a dynamic ankle splint incorporating a correction cradle. The correction cradle applies a torsional force to the foot, thus permitting correction of inversion and eversion of the ankle in conjunction with correction of dorsiflexion and plantar flexion. A dynamic wrist splint attaches to the forearm and provides a novel palm interface which adjusts to apply force over a large area of the palm depending on the angular position of the hand. A flexion strap is provided at the back of the hand for applying flexion forces.

In a preferred embodiment, a bi-directional power unit, which may employ a torsional spring, is fastened between first and second struts to selectively deliver force opposing either extension or flexion. The power unit is mounted about a hinge pin and can be rotated between two positions. In the first position, the power unit is locked relative to the first strut and the torsion spring opposes relative movement of the second strut in a first direction. In the second position, the power unit is locked relative to the second strut. In this second position, the torsion spring opposes movement of the first strut relative to the second strut. However, because of the rotation and re-locking of the power unit, the second position provides force in the opposite direction from the force provided in the first position. As a result, a single dynamic splint can be used in both flexion and extension modes.

Additional features of the dynamic splint include pivoting self-aligning contour plates on the struts that conform to the anatomy and provide a mechanical interlock to bony prominences on the patient's limbs, such as the malleoli and femoral condyles. As a result, superior bracing stability is achieved and the tendency of splints to migrate downward during ambulation is eliminated. A novel single cuff/strap design simplifies set-up and provides infinite adjustment capability for increased comfort and performance. Infinitely adjustable telescoping struts are also provided to facilitate custom fitting adjustment.

An improved cam locking mechanism disables the torsional force of the power unit when donning or doffing the splint. Significantly, this cam locking mechanism is also useful in locking the splint in a predetermined position to protect the affected limb against movement and damage during ambulation.

The dynamic splints disclosed permit maintenance of a defined tolerable force level with near constant linearity over a wide range of motion of a body joint. The dynamic splints are particularly useful for prophylactic maintenance of range-of-motion and mobility, particular in post-operative cases.

BRIEF DESCRIPTION OF THE DRAWINGS

FIG. 1 is a view in side elevation of the dynamic extension splint of the present invention;

FIG. 2 is a plan view of a strut assembly for the dynamic extension splint of FIG. 1;

FIG. 3 is a sectional view of the strut assembly of FIG. 2;

FIG. 4 is a view in from elevation of the strut assembly of FIG. 1;

FIG. 8 is a sectional view of the strut assembly of FIG. 2 showing a range of motion stop assembly;

FIG. 9 is a sectional view of a spring loaded pin used in the range of motion stop assembly of FIG. 8;

FIG. 10 is a partial plan view of the strut assembly of FIG. 8;

FIG. 11 is a partial plan view of a strut assembly for the dynamic extension splint of FIG. 6 showing a range of motion stop assembly;

FIG. 12 is a partial sectional view of the strut assembly of FIG. 11;

FIG. 13 is a side view of a locking pin according to the present invention, installed through the housing and into the strut assembly to prevent relative rotation of the struts;

FIG. 22A is an assembly drawing showing one side of a dynamic splint with pivoting contour plates and infinitely telescoping struts according to the present invention, and FIG. 22B is a detail drawing of a pivoting contour plate;

FIG. 26A shows the bi-directional power unit connected for flexion operation.

DESCRIPTION OF THE PREFERRED EMBODIMENTS

Figure 5:
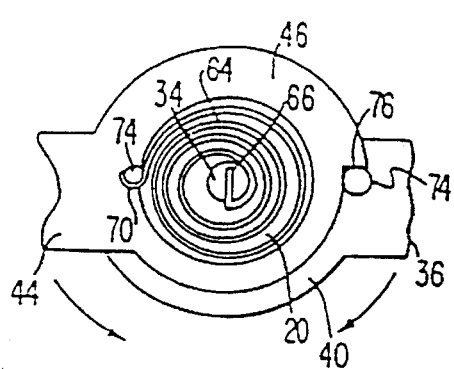
FIG. 5 is a sectional view of a biasing spring assembly used in the strut assembly of FIG. 3.

Referring now to FIGS. 1–5, the dynamic extension and/or flexion splint of the present invention indicated generally at 10 includes a suspension sleeve 12 formed from neoprene foam or similar material having some elasticity. The suspension sleeve is adapted to fit snugly around a limb or other body member in the area of a joint and operates to position a mechanical joint assembly 14 in alignment with a body joint. Suspension sleeve 12 provides a slight compression to the body member in the area of the affected body joint. This compression, and heat associated therewith, facilitates tissue nutrition which facilitates tissue growth.

A pair of mechanical joint assemblies 14 are mounted upon opposite sides of the suspension sleeve 12 as illustrated in FIG. 4, and each mechanical joint assembly includes first and second strut members 16 and 18 which extend outwardly from a mechanical joint 20 which is a hinge structure. The strut members 16 and 18 are removably received in open ended, spaced pockets 22 and 24, respectively, and a pair of such pockets are secured to each of two opposite sides of the suspension sleeve 12. These pockets may be formed of leather or similar material, and operate to facilitate removal of a mechanical joint assembly 14 therefrom. When the mechanical joint assembly is in place within the pockets 22 and 24, the mechanical joint 20 will be retained in position at the side of a body joint to be treated. Adjustable posterior straps 26 and 28 and anterior straps 30 and 32 are secured to the pockets 22 and 24. The combination of an anterior and posterior strap is positioned on either side of the mechanical joint 20, and these straps cooperate to surround the limb of a user on either side of a joint to be treated. Such anterior and posterior straps insure that optimum therapeutic effectiveness is obtained from the spring tension provided by the mechanical joint 20.

The mechanical joint 20 is formed at ends of the strut members 16 and 18 which are pivoted about a pivot post 34. These pivoted ends of the strut members are bifurcated to provide an enclosure for an adjustable spring mechanism used to tension the mechanical joint 20. Thus, the first strut member 16 consists of a flat, elongate strut section 36 which, as it approaches the mechanical joint 20, is split into an upper leg 38 and a lower leg 40. The upper leg extends parallel to and is spaced from the lower leg by a bridging section 42. Similarly, the second strut member 18 includes a flat, elongate strut section 44 having a bifurcated end with a lower leg 46 which extends parallel to but is spaced from an upper leg 48 by a bridging section 50. The upper and lower legs 38 and 40 and the upper and lower legs 46 and 48 are arcuate in configuration, as illustrated by the lower legs 40 and 46 shown in FIG. 5. The upper legs 38 and 48 substantially match the lower legs in configuration.

As illustrated in FIG. 3, the legs 46 and 48 fit within the legs 38 and 40, and are mounted for pivotal movement by the pivot post 34 which extends therethrough. This pivot post creams a pivotal axis which is substantially perpendicular to the longitudinal axes 52 and 54 of the strut sections 36 and 44, respectively.

A gear housing 56 is secured to the outermost surface of the upper leg 38, and operates to enclose a gear 58 mounted upon one end of the pivot post 34. This gear meshes with an adjustment screw 60 which is mounted for rotation in the gear housing 56. The adjustment screw has threads which engage the teeth of the gear 58 in known manner to rotate the gear and thereby rotate the pivot post 34. However, when the adjustment screw 60 is stationary, it locks the gear and the pivot post to the upper leg 38 and the lower leg 40. However, the lower leg 46 and upper leg 48 are mounted for pivotal movement about the pivot post 34.

As will be noted from FIG. 3, the pivot post extends completely through the upper legs 38 and 48 and the lower legs 40 and 46, and is held in place by a removable clip 62 which engages a groove in the pivot post. This removable clip may be formed by a spring clip, washer, or other known removable clip means, which can be removed from a groove in the pivot post 34 to facilitate disassembly of the mechanical joint 20. This permits a circular leaf-spring 64 to be mounted about the pivot post 34 between the lower and upper legs 46 and 48. One end 66 of this circular leaf-spring is secured within a central slot 68 formed in the pivot post 34, while an opposite end 70 of the leaf-spring is hooked about a post 72 which extends between the lower leg 46 and the upper leg 48. A second post 74 extends between the upper leg 38 and the lower leg 40, and this post is engaged by a step 76 formed in the periphery of the lower and upper legs 46 and 48 when the flat elongate strut sections 36 and 44 are in the extended position of FIG. 2.

The degree of tension set into the circular leaf-spring 64 may be indicated by indicia 132 on the gear 58 which cooperates with a stationary indicator 134 formed on the gear housing 56. Specifically, gear 58 may be marked about its periphery with a series of numbers or other markings indicating the relative tension existing on the spring when that marking occupies a defined position. Stationary indicator 134 may take the form of an aperture in gear housing 56 through which indicia 132 (i.e. the numbers or other markings) are visible.

As will be noted from FIG. 5, when the flat elongate strut sections 36 and 44 are pivoted toward one another in the direction of the arrows in FIG. 5, the steps 76 will move away from the post 74 and the pivotal movement will be opposed by the tension of the circular leaf-spring 64. Thus, the flat, elongate strut sections move from an extended position with the steps 76 in contact with the post 74 against the bias of the spring 64 to a second closed position wherein the first and second strut members come into contact and extend from the bottom side of the mechanical joint 20 in FIG. 5. As the flat elongate strut sections 36 and 44 are pivoted back to the extended position shown in FIG. 2, the pivotal movement is aided by the bias of the spring 64. It is obvious that this bias may be adjusted by rotating the adjustment screw 60 which in turn engages and rotates the gear 58 to rotate the pivot post 34. Depending upon the direction of rotation of the pivot post, the convolutions of the spring 64 will be tightened or loosened to adjust the bias of the spring.

It is noteworthy that the flat elongated strut sections 36 and 44 are formed from aluminum or similar lightweight, bendable material. Not only does this make the dynamic extension splint 10 light and compact, but it also permits the strut sections to be bent to conform to the outer contour of the limb of a user after the splint is in place to enhance comfort. Also, since the mechanical joint 20 can be disassembled by removing the spring clip 62, the spring 64 can be reversed to reverse the direction in which the spring aids or opposes pivotal movement. This facilitates therapeutic use of the dynamic extension splint 10 to provide either flexion or extension resistance. The spring force can also be reversed by the means described below in connection with FIGS. 23 through 27.

Figure 6:
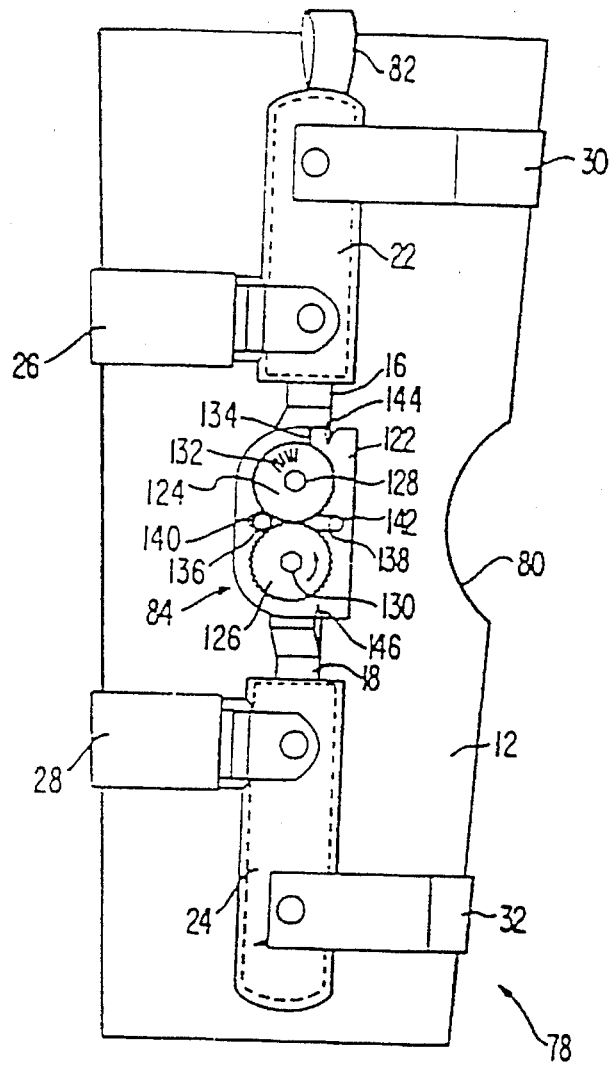
FIG. 6 is a view in side elevation of a second embodiment of the dynamic extension splint of the present invention.
Figure 7:
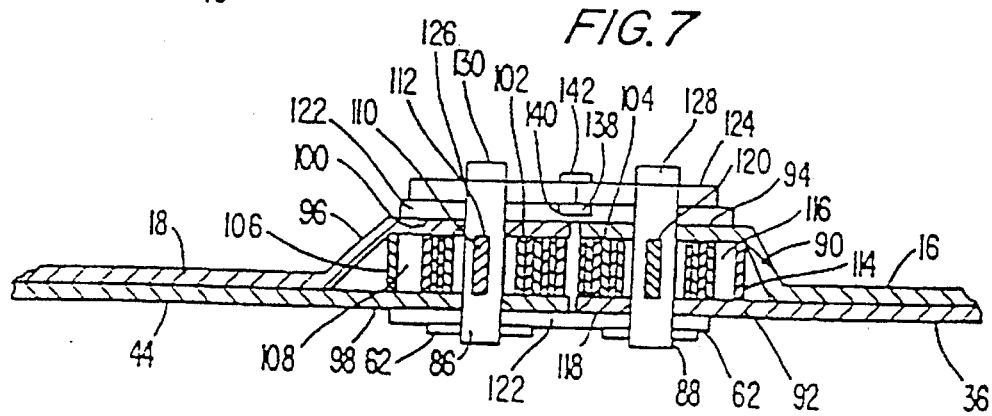
FIG. 7 is a sectional view of a strut assembly for the dynamic extension splint of FIG. 6.

Referring now to FIGS. 6 and 7, a second embodiment of the dynamic splint of the present invention is indicated generally at 78. For purposes of description, structural elements of dynamic splint 78 which are identical in structure and operation to those previously described in connection with dynamic splint 10 will be designated with like reference numerals. Also, in FIG. 6, only one side of dynamic splint 78 is illustrated, but it should be recognized that the first and second strut members and mechanical joint shown in FIG. 6 are provided on both sides of the suspension sleeve 12 as shown in FIG. 2.

Dynamic splint 78 includes a suspension sleeve 12 which differs from that of FIG. 1 in that it is provided with an opening 80 to receive the patella or another portion of a body joint to be treated. The sleeve also includes pull straps on either side connected to one end of the pocket 22. These pull straps, one of which is indicated at 82, are used to pull the sleeve 12 over a limb or a body member.

Dynamic splint 78 differs from dynamic splint 10 mainly in the structure of the mechanical joint, for the splint 78 includes a polycentric mechanical joint 84. This polycentric joint includes two spaced pivot pins 86 and 88 instead of the single pivot post 34 of FIG. 3. Each of these pivot pins extends through one of the bifurcated ends of the strut members 16 and 18. It will be noted that these bifurcated ends do not overlap, as illustrated in FIG. 3, but instead, are spaced apart by the pivot pins 86 and 88. Thus, as illustrated in FIG. 7, the first strut member 16 includes the flat elongate strut section 36, and a bridging section 90 which extends between a lower leg 92 and an upper leg 94. Similarly, the second strut member 18 includes the flat, elongate strut section 44 and a bridging section 96 which extends between a lower leg 98 and an upper leg 100. The bridging sections 90 and 96 space the lower legs 92 and 98 an equal distance from the upper legs 94 and 100, and circular leaf-springs 102 and 104 are mounted about the pivot pins 86 and 88 between the upper and lower legs of the first and second strut members. One end 106 of the spring 102 is hooked about a post 108 that extends between the lower leg 98 and the upper leg 100 of the second strut member 18, while an opposite end 110 of the spring 102 is secured within a slot 112 formed in the pivot pin 86. Similarly, one end 114 of the spring 104 is hooked about a post 116 which extends between the lower leg 92 and upper leg 94 of the first strut member 16, while a second end 118 of the spring is secured within a slot 120 formed in the pivot pin 88.

A housing 122 extends over the bifurcated ends of the first and second strut members 16 and 18 and encloses the polycentric mechanical joint 84. The pivot pins 86 and 88 extend outwardly on either side of the housing and on one side are clipped in place by the removable clips 62. The opposite ends of the pivot pins extend outwardly beyond the housing 122, and bear meshed gear members 124 and 126. These gear members operate to gear the pivot pins 86 and 88 together, and one gear member is mounted on the end of each of the pivot pins to rotate therewith. Secured to the end of each pivot pin and projecting above the respective gear members 124 and 126 is a tool engaging adjustment knob, with two such adjustment knobs being indicated at 128 and 130. These adjustment knobs include a plurality of flat surfaces for engagement with a wrench-type tool that is used to turn the gear members 124 and 126. For example, if the tool engages the adjustment knob 130 and turns the gear 126 in the direction of the arrow in FIG. 6, then both of the pivot pins 86 and 88 are turned by an equal amount due to the mesh between the gears 126 and 128. This adjusts the bias of the springs 102 and 104 an equal amount, and the degree of tension set into the springs may be indicated by indicia 132 on the gear member 124 which cooperates with a stationary indicator 134 formed on the housing 122.

To lock the gear members 124 and 126 in a desired position, a small locking gear 136 is provided on the end of an elongate slide member 138 which slides in a slot 140 formed in the housing 122. The locking gear 136 has teeth which engage the teeth of the gear members 124 and 126 to lock these gears in place. To unlock these gears for purposes of bias adjustment, the slide member 138 is moved to the left in FIG. 6 to disengage the gear 136. The slide member may be manipulated by means of a knob 142 provided on the end thereof opposite to the locking gear 136.

The housing 122 is formed with indentations 144 and 146 to engage the first and second strut members 16 and 18. These indentations provide stops for the strut members in the extended position shown in FIG. 6. However, the two strut members may be moved together to the left in FIG. 6 for a full 180° due to the polycentric construction of the mechanical joint 84. As the strut members pivot, the pivotal movement is transmitted by the posts 108 and 116 to the springs 102 and 104, and these springs oppose pivotal movement between an extended and a closed position in one direction while aiding pivotal movement in the opposite direction. The bias of the two springs may be adjusted equally by rotating one of the gear members 124 or 126 to accomplish rotation of the opposite gear for an equal amount and therefore rotation of the pivot pins 86 and 88.

As in the case of the spring 64, the springs 102 and 104 can be reversed by removing the clips 62 and disassembling the mechanical joint 84. Thus the dynamic extension splint 78 can be configured to provide either flexion or extension resistance.

The dynamic extension splints 10 and 78 may be provided with an adjustable range of motion stop assembly to limit the degree of motion a body member is permitted to make around a body joint. For many types of injuries, it is beneficial to rehabilitate the body joint in stages with the degree of motion permitted by the splints being increased as free motion in a previous stage is achieved. With reference to FIGS. 8–10, the mechanical joint assembly 14 for the dynamic extension splint 10 includes an arcuate line of spaced holes 150 and 152 formed in the legs 38 and 40 respectively. A hole 150 is aligned with a corresponding hole 152 to receive one of the spring biased pins 154 or 156 extending from opposite ends of a stop 158. The stop 158 includes a stop housing 160 that retains the pins 154 and 156 which are biased outwardly from the ends of the stop housing by a spring 162. The stop housing extends across the legs 46 and 48 so that when the pins extend into selected holes 150 and 152, the stop 158 will engage the legs 46 and 48 to limit the relative pivotal movement of the strut members 16 and 18. To remove or adjust the position of the stop 158, the pins 154 and 156 are compressed into the stop housing 160 so that the stop can be disengaged from the holes 150 and 152.

The dynamic extension splint 78 shown in FIGS. 11 and 12 is also provided with a range of motion stop assembly including a plurality of arcuately arranged spaced holes 164 and 166 formed in the upper and lower edges respectively of the housing 122. As shown in FIG. 12, which is a view of a portion of the mechanical joint 84 with the springs 102 and 104 removed for purposes of illustration, two stops 158 are positioned to span the distance between the upper and lower edges of the housing 122, with a stop extending in front of each of the bifurcated ends of the strut members 16 and 18. The spring biased pins 154 and 156 for each stop extend into a hole 164 and 166 respectively in the housing 122. Thus, each stop limits the range of pivotal movement of a strut member 16 or 18 depending upon where the stop is positioned in the line of holes 164 or 166.

FIG. 13 is an exploded view of a preferred embodiment of the mechanical joint 20 which provides a locking means for relieving the action of the bias mechanism during installation and removal of dynamic extension splint 10. In this embodiment, mechanical joint 20 has a hole 170 through housing 56 of mechanical joint 20. A hole 172 of size and shape similar to that of hole 170 is formed in strut member 18, which rotates relative to housing 56 and strut member 16 as explained previously. Holes 170 and 172 are formed at the same distance from the axis of rotation of strut member 18 (i.e. pivot post 34, not shown) so that holes 170 and 172 are aligned, at one point in the rotation of strut member 18 relative to housing 56, along a locking pin insertion axis 174 parallel to the axis of rotation of strut member 18. At the point of alignment of holes 170 and 172, locking pin 176 can be inserted through both holes 170 and 172 to prevent relative motion of strut members 16 and 18. Locking pin 176 comprises knob 178 and elongated pin 180. Of course, a plurality of holes 170 or holes 172 could also be provided to provide several points of alignment at which strut members 16 and 18 could be locked together. Also, holes 170 and 172 and locking pin 176 can be provided on either one or both of the two mechanical joints 20 of a given dynamic extension splint 10, as desired.

In use, locking pin 176, together with holes 170 and 172, can be used to remove the bias force provided by mechanical joint 20 during attachment and removal of dynamic extension splint 10 from the affected body part. The elimination of the bias force during attachment and removal simplifies the attachment and removal process, particularly when larger bias forces are being applied. Specifically, any bias force components tending to act against the forces needed to disengage components of dynamic extension splint 10 from the affected body part will be neutralized. This neutralization of bias forces also prevents any springing back of strut members 16 or 18 when one of strut members 16 or 18 is released from the affected body part and the other is still attached. Such springing action as a result of bias forces during removal of the device could aggravate the injuries being treated with dynamic extension splint 10, or cause further injuries. Of course, bias force could also be reduced by adjusting the tension on mechanical joints 20. However, the use of locking pin 176 permits complete elimination of the bias force without disturbing the desired bias force setting.

Figure 14:
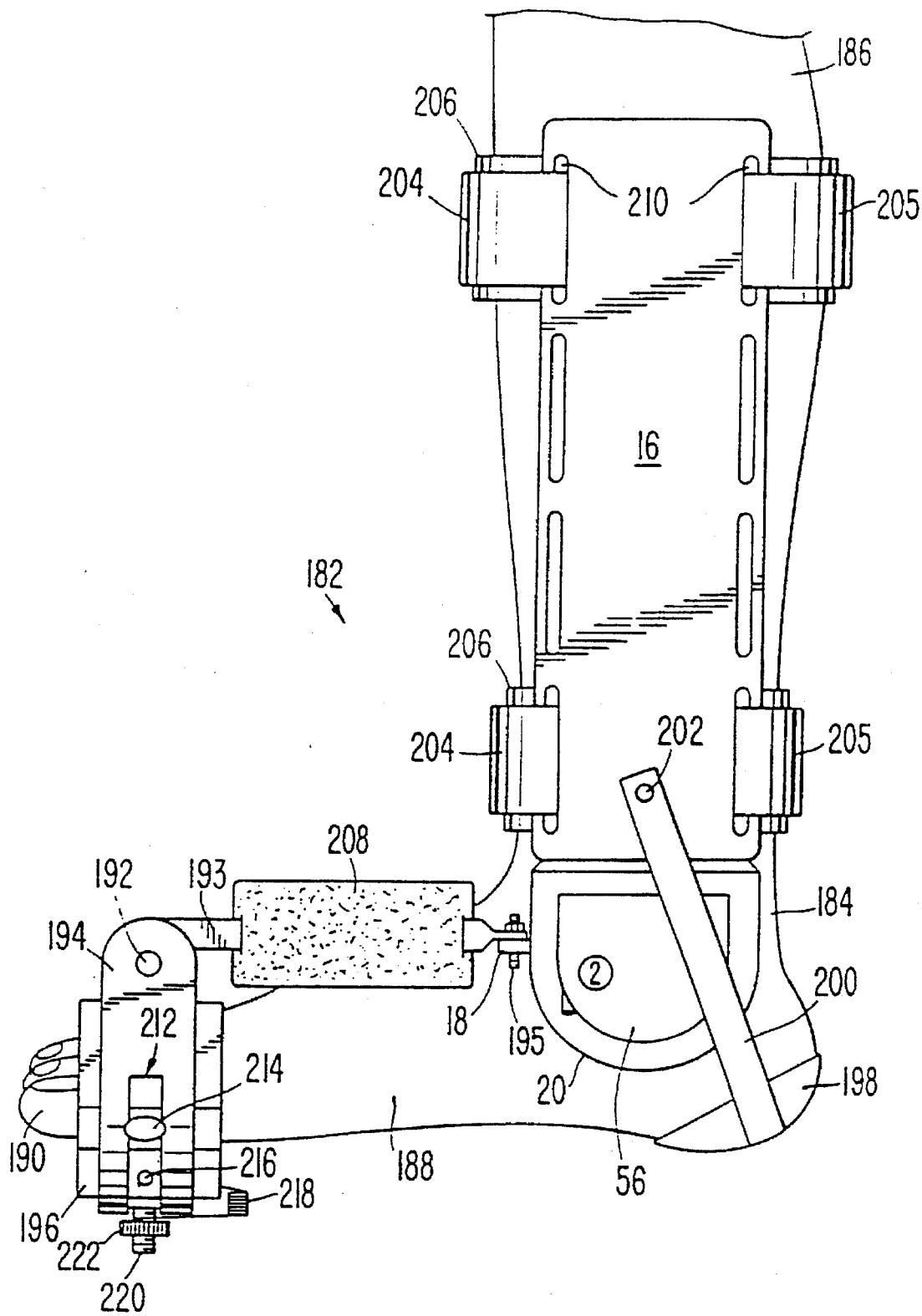
FIG. 14 is a side elevation of an ankle brace according to the present invention incorporating a novel foot pronation/supination cradle.

Referring now to FIG. 14, an ankle splint according to the present invention is shown generally at 182, attached to a human ankle 184 connecting leg 186 to foot 188 having toes 190. Ankle splint 182 comprises two strut members 16, one on each side of leg 186, which are rotatably connected via mechanical joints 20 (which is of a type described previously) to strut members 18, one on each side. Strut members 18 are rotatably connected by fasteners 195 to arms 193 which are rotatably connected by pins 192 to a central cradle 194 which supports a foot carriage 196. Foot carriage 196 is connected to travel in an arc relative to cradle 194 along slot 212. Fasteners 214 loosely connect foot carriage 196 to cradle 194 to permit this arc-like movement. Fasteners 214 are preferably of nylon or incorporate nylon beating washers to facilitate sliding of carriage 196 along slot 212. A spring 218 is mounted between attachment 216 (mounted on carriage 196) and a tensioning bolt 220 mounted through slot 212 and held in position along slot 212 by nut 222.

Fasteners 195 can be loosened to laterally adjust the angle of arms 193 to compensate for deviations in alignment of the foot. Fasteners 195 will then be tightened to hold arms 193 firmly to strut members 18.

Strut members 16 are attached to leg 186 by extension straps 204 and flexion straps 205 which pass through opposite holes 210 at the front and back respectively of one of the two strut members 16, and are then attached to similar straps 204 and 205 associated in the same manner with the strut member 16 on the other side of leg 186. The attachment of straps 204 and 205 is preferably by hook-and-loop fasteners, such as Velcro, although other types of strap connecting hardware could also be used. Optionally, a heel cup 198 may be provided for further stabilizing ankle splint 182 with respect to ankle 184. A strap 200 connects heel cup 198 to ankle splint 182 via a snap 202 or other appropriate fastening means. Cuffs 206 are installed on leg 186 under straps 204 to prevent chafing and increase comfort during use. Cuffs 206 are made from a three-part laminate comprising a central layer of split neoprene, an outer layer of loop material for use with hook-and-loop fasteners, and an inner non-allergenic padding and lining layer. Cuffs 206 have loop fastener material section 207 attached to the inner layer of cuffs 206 at an edge 211 thereof parallel to the longitudinal axes of strut members 16. Cuffs 206 will be provided in an oversize circumference, and may then be cut at the end opposite from edge 211 bearing loop fastener material section 207, to fit the particular patient's body part. Loop fastener material section 207 will engage the outer layer of cuffs 206 at any point about cuffs 206, thus providing a continuously-adjustable snug fit around leg 186. Strut member 18 may be provided with a pad 208 of sheepskin or other soft material. Strut members 16 are of aluminum or other relatively soft metal to facilitate bending of strut members 16 by the installer to conform to the shape of leg 186.

Figure 15:
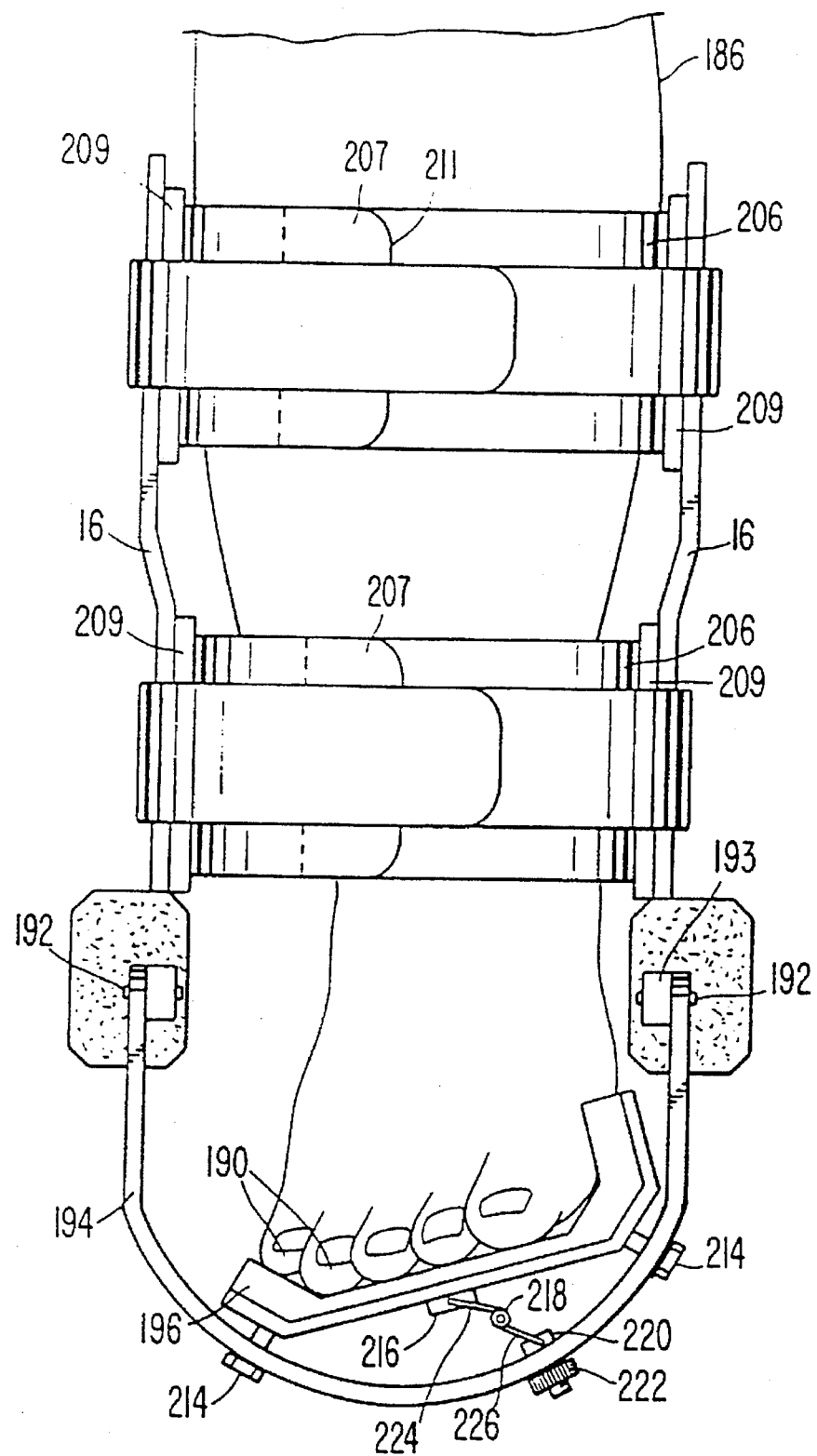
FIG. 15 is a front elevation of the ankle brace of FIG. 14.

FIG. 15, which is a frontal view of ankle splint 182, shows more clearly the bending of strut member 16 to conform strut member 16 to the shape of leg 186. As a further attachment means, strut members 16 have hook fastener material 209 attached to their inner surfaces, and hook fastener material 209 engages the loop fastener material on the outer layers of cuffs 206 to hold strut members 16 in position with respect to cuffs 206. Carriage 196 receives the ball of foot 188. Of course, the configuration of cuffs 206 can be changed depending on the application. Either a plurality of smaller cuffs 206 or one larger cuff 206 can be provided in the mounting area of ankle splint 182.

Ankle splint 182, through the bias force provided by mechanical joints 20, provides therapy for correction of both plantar flexion and dorsiflexion limitations. As will be seen, the bias force provided by spring 218 acting on carriage 196 also permits correction of inversion and eversion of the foot. Since inversion or eversion accompany a large percentage of ankle abnormalities, ankle splint 182 provides a major advance in total dynamic therapy for the lower leg, ankle, and foot.

Referring now to FIG. 15, it will be seen that spring 218 is of the type having two arms 224 and 226 extending outwardly from a central biasing device, such as a wire coil, which provides a force biasing arms 224 and 226 toward a rest position in which arms 224 and 226 are separated. Arm 224 is connected to attachment 216 of carriage 196, and arm 226 is connected to tensioning bolt 220. The arms 224 and 226 may pass through holes provided in attachment 216 and tensioning bolt 220, or may be attached in some other appropriate way. Depending on the positioning of tensioning bolt 220 anywhere along slot 212, spring 218 provides a variable biasing force tending to move carriage 196 in one or the other direction along slot 212. As carriage 196 moves along slot 212, it rotates in an arc relative to ankle 184, tending to rotate the end of foot 188 in the region of toes 190 relative to ankle 184. Also, due to the shape of cradle 194, the ball of the foot 188 tends to move up or down relative to ankle 184 as it rotates under the influence of spring 218. Thus, cradle 194, carriage 196, spring 218, and their associated components, in conjunction with the other components of ankle splint 182, comprise a means for applying a bias force tending to rotate foot 188 laterally relative to ankle 184, while at the same time applying a bias force tending to move the end of foot 188 up or down relative to ankle 184. The cradle 194 is designed to be reversible in its connection to arms 193 to accommodate both left and right feet.

Figure 16:
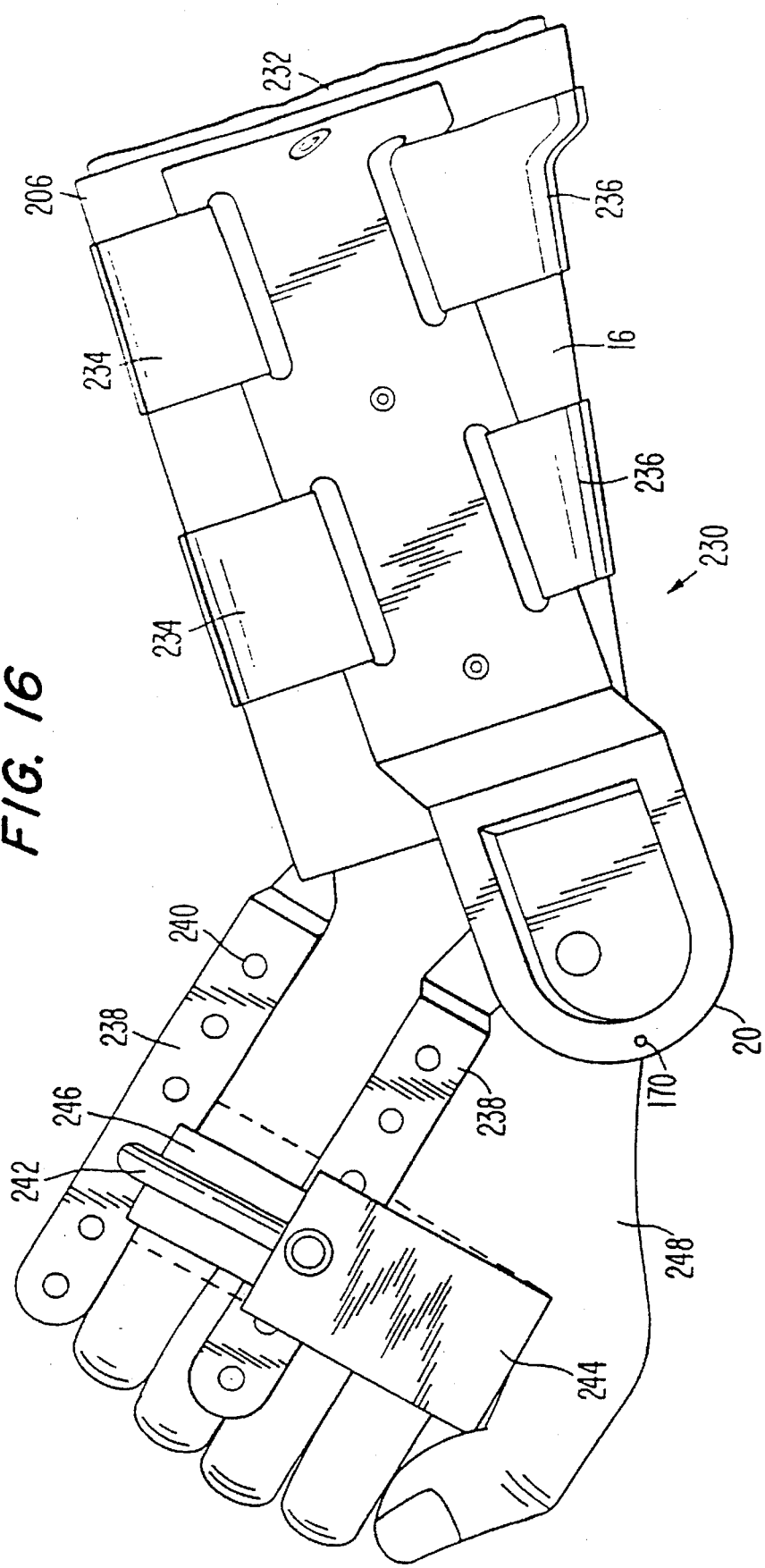
FIG. 16 is a side view of a wrist brace according to the present invention incorporating a novel palm interface structure.

FIG. 16 shows a wrist splint 230 designed according to the invention. An elastic neoprene cuff 206 similar to the cuffs 206 described previously is attached about forearm 232, and flexion straps 234 and extension straps 236 are attached about cuff 206, using hook-and-loop fastener material or other adjustable attaching methods, to connect two strut members 16 located on the sides of forearm 232. Each strut member 16 is fixed to a mechanical joint 20. Struts 238 are attached to mechanical joint 20 to rotate relative thereto and to be biased in one direction or the other depending on the assembly of mechanical joint 20, as described previously. Each strut 238 has a series of adjustment holes 240 spaced along its length. Depending on the size of the patient's hand 248, axial pin 242 will be installed through and between two corresponding adjustment holes 240, one on each strut 238. Axial pin 242 is a structural member which connects struts 238 to hold struts 238 parallel. Axial pin 242 also provides an attaching point for a palm strap 244, and defines an axis about which palm strap 244 rotates. Strap 246 is attached to axial pin 242 or palm strap 244 across the back of hand 248. In this embodiment, straps 244 and 246 are preferably made of fairly rigid material, such as thin aluminum. In actual use, straps 244 and 246 will be padded for comfort with sheepskin or other appropriate padding material as described previously with respect to other embodiments. However, to avoid obscuring structural parts in the drawing, this padding material is not shown in FIG. 16.

In use, palm strap 244 transmits the bias force of mechanical joints 20, where appropriate, to oppose extension of the wrist. Significantly, the distance between palm strap 244 and mechanical joint 20 is adjustable by installation of axial pin 242 in different pairs of adjustment holes 240. Also, palm strap 244 rotates about axial pin 242 during extension of the wrist, so that palm strap 244 maintains its location relative to the palm of hand 248. This rotating action is important, since the distance between the palm and mechanical joints 20 will vary during movement of the hand about the axis extending between mechanical joints 20. The rotating motion of palm strap 244 provides a means for dynamically adjusting the location of palm strap 244 in the palm in response to changes in the orientation of hand 248.

Strap 246 transmits the bias force of mechanical joints 20 to oppose flexion of the wrist when mechanical joints 20 are adjusted to provide a flexion-opposing bias force.

Figure 17:
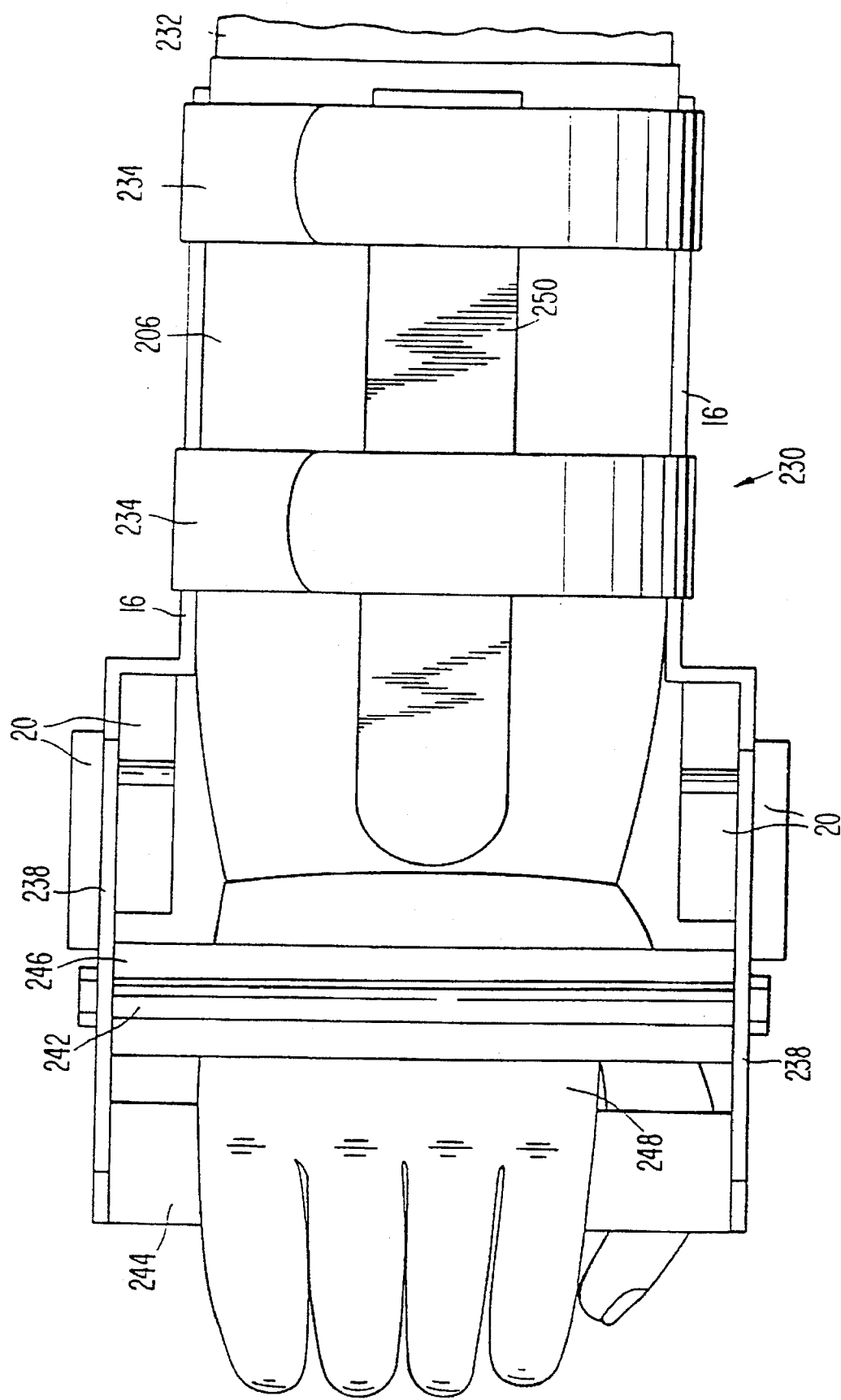
FIG. 17 is a top view of the wrist brace of FIG. 16.

FIG. 17 is a top view of the wrist splint 230 of FIG. 16 showing a dorsal support 250 mounted along the dorsal side of forearm 232 and held in place by flexion straps 234. The rounded end of dorsal support 250 is placed immediately to the side of the styloid process, toward the center of the wrist. Preferably, dorsal support 250 has hook fastener material mounted on its underside to connect with the loop fastener material on the exterior of cuff 206, thus further holding dorsal support 250 in place relative to the wrist. Dorsal support 250 is of aluminum or other bendable rigid material. Dorsal support 250 provides additional rigidity and support for the attachment of wrist splint 230 to forearm 232 when wrist splint 230 is applied to oppose extension of the wrist. In particular, during extension of the wrist, the dorsal support 250 delivers the counterforce of the wrist splint 230 to the wrist axis at an optimal point. Dorsal support 250 will not be used when wrist splint 230 is configured to oppose flexion of the wrist.

Figure 18:
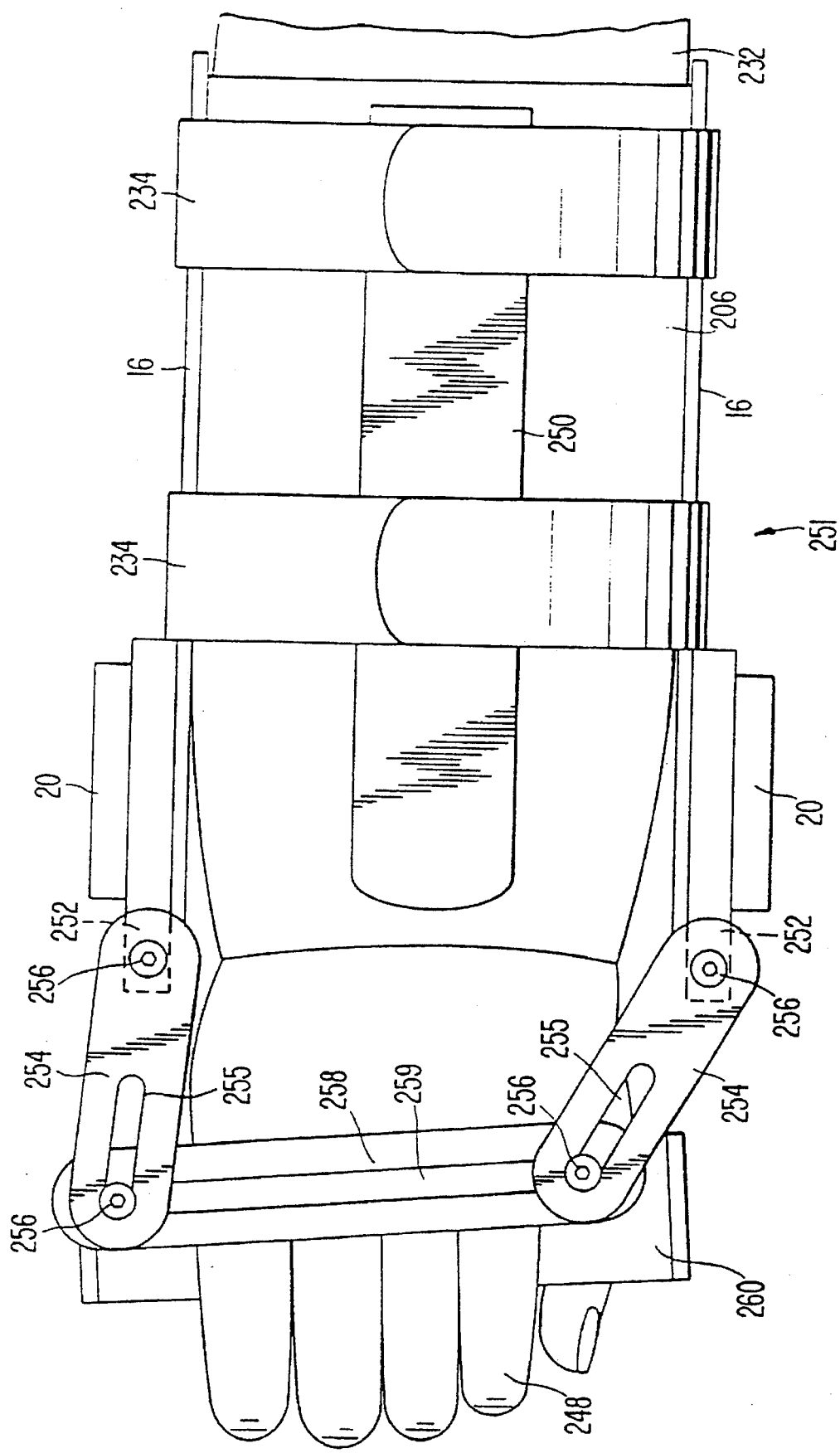
FIG. 18 is a top view of another embodiment of the wrist brace of the present invention, incorporating a modified palm interface design.

FIG. 18 shows a preferred embodiment of a wrist splint generally at 251. The attachment of wrist splint 251 to forearm 232 is substantially similar to that previously described with reference to FIGS. 16 and 17 for wrist splint 230, and will not be repeated here. Wrist splint 251 differs from wrist splint 230 in that relatively short strut members 252 are attached to mechanical joints 20 to rotate relative thereto, biased by the bias force exerted by mechanical joint 20 as described previously. Elongated rigid arms 254 are attached to each of the strut members 252 through one end of arms 254 by fasteners 256. Fasteners 256 may be hex head screws, and are chosen so that they may be loosened, permitting arms 254 to rotate about the axis defined by the length of fasteners 256, and then tightened to hold arms 254 at a desired angle with respect to strut members 252.

The ends of arms 254 not attached to strut members 252 are attached through slots 255 to opposite ends of an elongated rigid crossbar 258 through slot 259 by additional fasteners 256 which, as described above, can be loosened to permit adjustment of the angles between arms 254 and crossbar 258, and tightened to hold arms 254 and crossbar 258 relatively immobile. A palm strap 260 is attached at opposite ends to opposite ends of crossbar 258 to rotate about an axis parallel to the central longitudinal axis of crossbar 258. The adjustments provided by slots 255 and 259 permit adjustment of the length of the moment arm from the wrist axis to the palmar crease to suit the individual patient. In addition, the angular adjustability of the structure shown allows compensation for radial and ulnar deviation.

Figure 19:
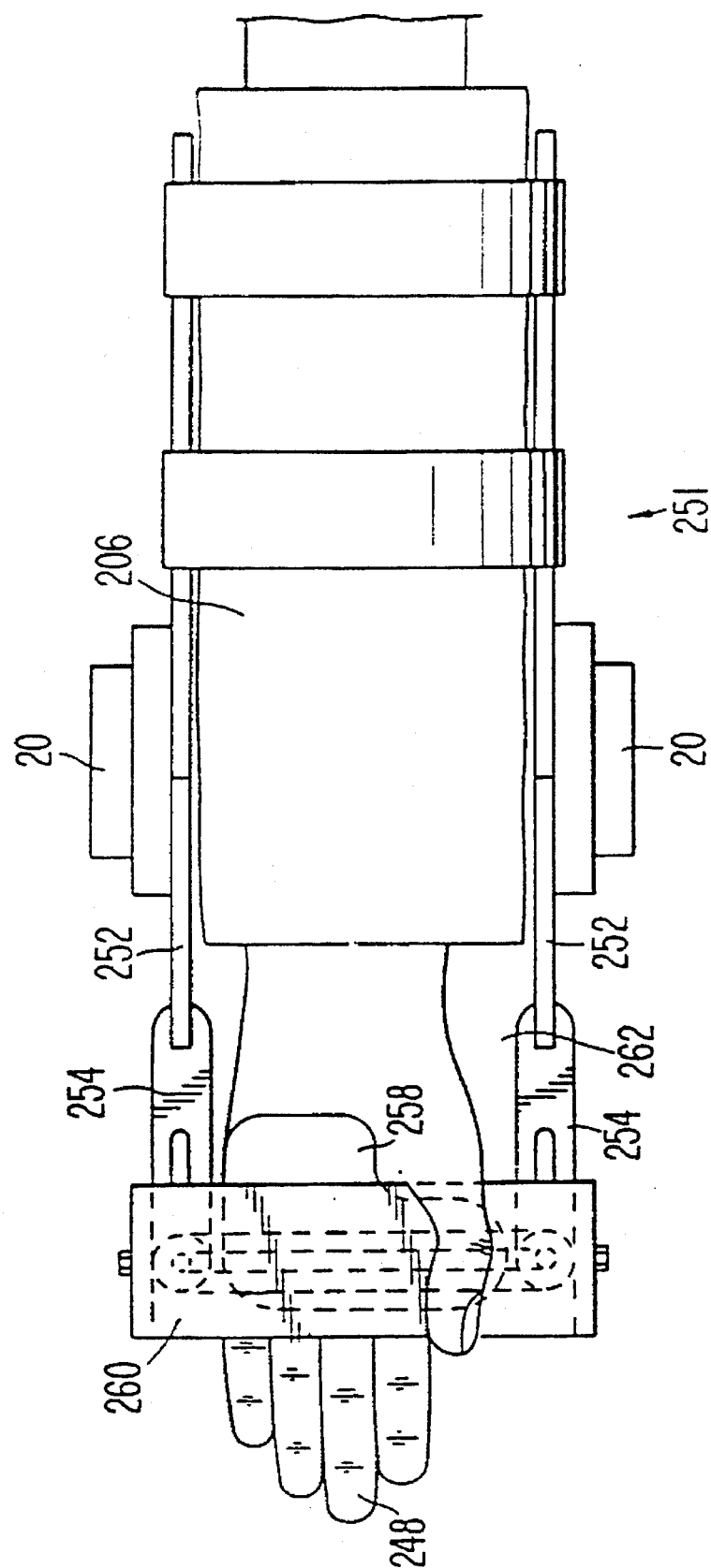
FIG. 19 is a bottom view of the wrist brace of FIG. 18 showing the palm interface thereof in greater detail.

FIG. 19 is a bottom view of wrist splint 251 of FIG. 18 and shows the palm interface of wrist splint 251 in greater detail. Palm strap 260 is a flexible strap, which may be made from heavy nylon fabric and provided with metal fasteners or snaps for rotatable attachment to crossbar 258. A palm pad 262, shaped to fit the palm with a cutout region to accommodate the thumb, is attached to palm strap 260. Palm pad 262 is preferably made of a fairly rigid yet flexible material, such as urethane. Palm strap 260 and palm pad 262 may be reinforced with thin aluminum inserts to provide added rigidity and structural strength. The aluminum inserts can be bent to provide a uniform loading across the concave surface of the transverse arch. Palm strap 260, palm pad 262, and crossbar 258 will generally be covered with lambs wool or other padding material (not shown) when wrist splint 251 is in use.

In use, the wrist splint 251 shown in FIGS. 18 and 19 can be adjusted to compensate for differences in angle between hand 248 and forearm 232 by adjusting the relative angles of strut members 252, arms 254, and crossbar 258 before tightening fasteners 256. As an additional comfort feature, palm pad 262 provides a means for distributing the bias force provided by mechanical joints 20 over a larger area of the palm. The flexible characteristics of palm strap 260 and palm pad 262 combine with the rotation of palm strap 260 relative to crossbar 258 to provide a dynamically self-adjusting force distribution apparatus throughout the range of motion of hand 248.

It is a particular feature of all of the designs discussed and shown previously that the split cuffs and straps are not located on the joint itself. Thus, counterforces are never applied directly to the joint. In many cases, the affected joint will have been injured and may be painful or swollen. Thus, this feature permits use of the dynamic splint of the present invention even during the early recovery stages of an injury to the affected joint. As noted previously, the mechanical joints in the dynamic splints of the present invention preferably allow full range of motion of the affected joint, plus 10% in either direction. This design provides a substantial advantage in that the joint is not immobilized during use of the splints, and everyday activities can be performed if necessary while wearing the splints. Full movement of the affected body parts during wearing of the splints enhances blood flow and thus tissue health. In addition, a full range of motion prevents stiffness in the direction other than that being treated. Thus, the dynamic splints of the present invention will not create a flexion limitation by limiting motion in the flexion direction during treatment of an extension problem.

FIG. 20 shows a cam locking mechanism 270 which is particularly useful with the dynamic splint of the present invention. Cam locking mechanism 270 comprises a first strut 274, pin receiving detents 272, pivot pin 276, second strut 278, housing member 280, cam 282, locking pin 284, elastomeric O-ring or rubber band 286, camshaft 288, locking knob 290, and attachment posts 292. The cam locking mechanism 270 will preferably be integrated with a force mechanism of the type disclosed above or a bi-directional force mechanism operating about pivot pin 276, but for the sake of clarity the force mechanism is omitted from the view in FIG. 20.

Figure 20B:
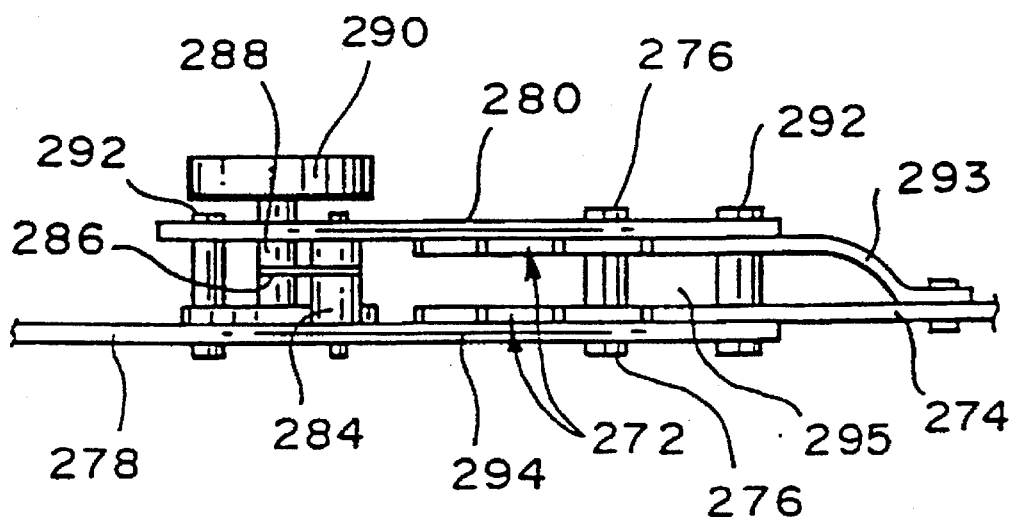
FIG. 20B is a side view of the cam locking mechanism shown in FIG. 20A.
Figure 20A:
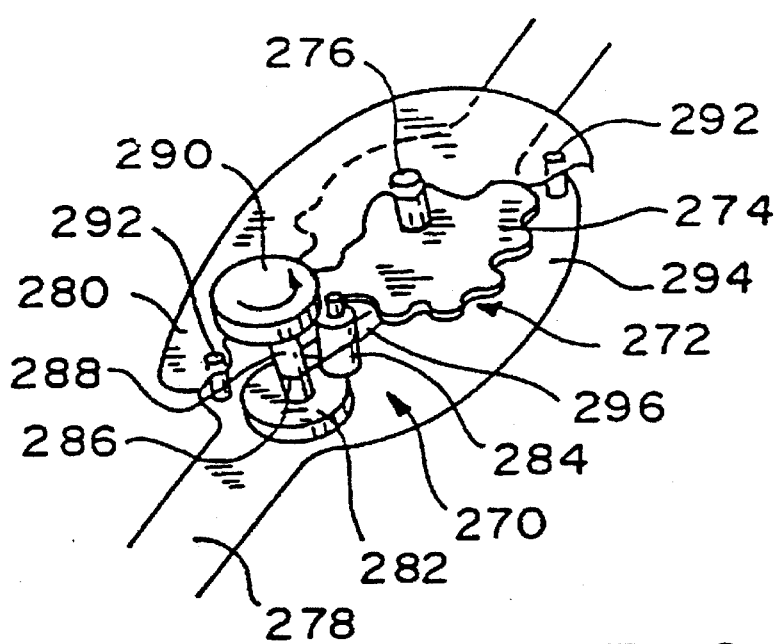
FIG. 20A is an assembly drawing of an improved cam locking mechanism for a dynamic splint.

Housing member 280, along with a housing member 294 attached to or formed integrally with second strut 278, serves to enclose the operating parts of cam locking mechanism 270. Housing member 280 is fixed to second strut 278 and spaced therefrom by a plurality of attachment posts 292. Pivot pin 276 is held in place between second strut 278 and housing member 280, either through attachment to second strut 278 and housing member 280 or preferably by floating insertion in holes provided in these two parts. A plurality of pin receiving detents 272 are disposed periodically about first strut 274, which may be either a proximal or distal strut of the splint. Pin receiving detents 272 are provided on first strut 274 adjacent housing member 294 as shown in FIG. 20. Preferably, another set of pin receiving detents 272 similar in appearance to the detents shown is attached to first strut 274 in parallel, spaced relationship with the pin receiving detents shown, so that the second set of pin receiving detents is adjacent housing member 280. In this way, locking pin 284 is held at each end by a detent 272 when the cam locking mechanism 270 is actuated. Although two sets of detents are preferred, for the sake of clarity, only one set of detents 272 is shown in FIG. 20A. FIG. 20B is a side view of the mechanism of FIG. 20 showing the second set of detents 272 provided on strut part 293 which is fixed to strut 274 by rivets or other suitable attachments. The spring of the adjustable force spring device of the present invention may be located in area 295 between strut 274 and strut part 293 around pivot pin 276 in the manner described elsewhere in the specification. Again, the details of the adjustable force spring device are omitted from FIG. 20B in order to more clearly show the parts and operation of the cam locking mechanism 270.

An elongated slot 296 is provided in housing member 294 and a corresponding elongated slot is provided in housing member 280 (not shown). Locking pin 284 extends between housing members 280 and 294 and is held therebetween. The ends of locking pin 284 reside in elongated slot 296 and the corresponding elongated slot in housing member 280, permitting translation movement of locking pin 284 along the elongated slots. Cam 282 is fixed to camshaft 288 which is rotatably attached to housing members 280 and 294 respectively. Camshaft 288 passes through housing member 280 and locking knob 290 is fixed to camshaft 288 on the outside of housing member 280. Cam 282 is shaped so that as cam 282 is revolved, locking pin 284 is forced to move along the elongated slots into locking engagement with one of the pin receiving detents 272. Preferably, the cam 282 on one side of the splint is constructed as a mirror image of the cam 282 on the opposite side of the same splint. In this way, one of the cams will be actuated by counterclockwise rotation and the cam on the opposite side of the limb will be actuated by clockwise rotation. In this way, turning both locking knobs 290 forward will lock both sides of the splint, and turning the knobs backward will unlock the splint. It has been found empirically that this mode of operation is more intuitive for patients than having the knobs both turn counterclockwise or both turn clockwise.

Rubber band 286 biases locking pin 284 against cam 282, so that locking pin 284 is held away from pin receiving detents 272 except when cam 282 is turned to force locking pin 284 into engagement with pin receiving detents 272. Thus, by turning the locking knob 290, the patient can activate cam locking mechanism 270 to lock the relative positions of the struts 274 and 278 in one of a plurality of predetermined positions. The cam locking mechanism 270 is particularly useful in disabling the torsional force of the power unit when donning or doffing the splint. Significantly, this cam locking mechanism is also useful in locking the splint in a predetermined position to protect the affected limb against movement and damage during ambulation. In many cases, it may be desirable to prevent any movement of the affected joint while the patient is moving around. For example, in some cases walking on an injured knee joint might result in pain or further damage if recovery has not progressed to the point where the joint can bear the forces of ambulation. In such cases, it may be preferable to lock the splint to prevent any flexion or extension of the leg if the patient will be walking with the splint installed. The struts can then be easily unlocked to apply force to the joint after the patient is sitting down and ready for therapy. Cam locking mechanism 270 is advantageous over the pin locking mechanism disclosed above in that it is self-contained and has no removable parts which could become lost or fall out during ambulation. Cam locking mechanism 270 has excellent structural strength and can thus be locked to bear the weight of the patient during ambulation and prevent movement, facilitating the advantageous mode of use described above.

Figure 21:
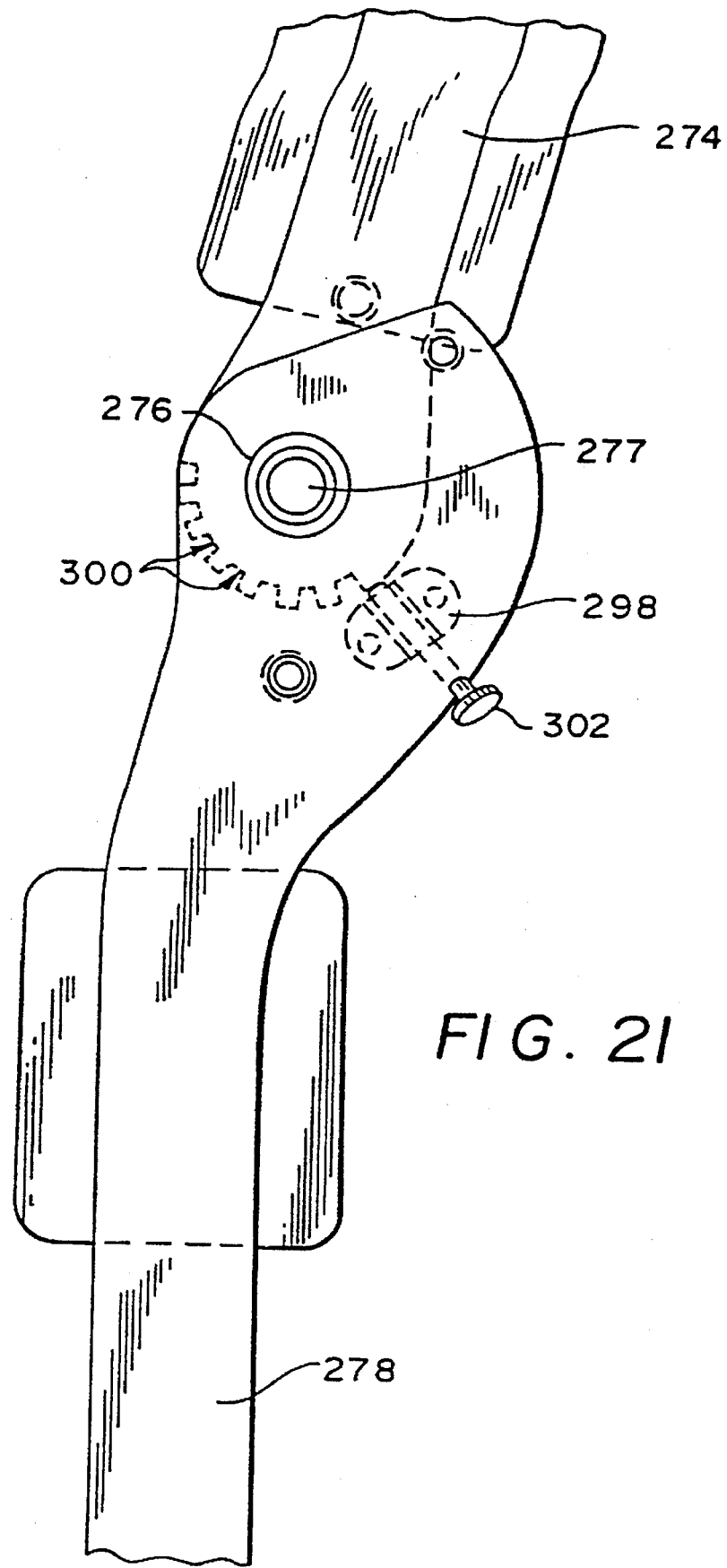
FIG. 21 is an assembly drawing of an alternative design locking mechanism for a dynamic splint.

FIG. 21 shows an alternative design locking mechanism for a dynamic splint. As shown in FIG. 21, struts 278 and 274 are connected for mutual rotation about pivot mechanism 276. Pivot mechanism 276 is preferably a hollow pivot mechanism with a central hole 277 sized to receive pivot post 34. Strut 274 is provided with detents 300 at predetermined locations radially spaced about pivot mechanism 276. Detents 300 are similar to the detents 272 shown in FIG. 20, but detents 300 are generally rectangular in shape to receive the flat end of cylindrical locking pin 302, in contrast to the sprocket shape of detents 272 which is adapted to receive the cylindrical cross-section of locking pin 284. Locking pin 302 is held against strut 278 by locking pin sleeve 298. Locking pin 302 may be spring loaded in the inward direction and provided with a means for selectively mechanically holding it in an outward position. For example, a tab can be provided on the knob portion of locking pin 302 to engage the edge of strut 278 when locking pin 302 is pulled out and rotated to engage the tab with the strut. In this way, the tab will mechanically hold the locking pin 302 in an outward position. By rotating locking pin 302, the tab can be disengaged from the strut and the spring force will urge the pin 302 into engagement with detents 300. When locking pin 302 moves inward, it engages one of the detents 300 and locks struts 274 and 278 together. When locking pin 302 is held in an outward position to clear detents 300, relative movement of struts 274 and 278 is possible.

FIG. 22A illustrates a preferred embodiment of a dynamic splint according to the present invention. As shown in FIG. 22A, dynamic splint side 304 comprises distal strut 306, proximal strut 308, tension unit 310, proximal strut extension 311, distal strut extension 320, pivot brackets 318 and 322, and pivot assemblies 324 installed on each of the pivot brackets 318 and 322. In the preferred embodiment, there are two pivot brackets 318 on the proximal end of the splint and three pivot brackets on the distal end. To provide a more clear illustration of the pivot brackets 318 and 322 and the mounting of the proximal and distal strut extensions, only one pivot assembly 324 is shown in the Figure, but it will be understood that pivot assemblies 324 are provided on each of the pivot brackets 318 and 322.

Tension unit 310 is preferably a force-adjustable tension unit constructed with a circular leaf spring, as described in detail elsewhere in the disclosure. Tension unit 310 may also have bi-directional force capability as disclosed below with reference to FIG. 23. Tension unit 310 connects proximal strut 308 and distal strut 306 about a pivot pin and applies a force opposing pivotal relative movement of the struts in one direction and aiding pivotal relative movement of the struts in another direction. The splint side 304 shown in FIG. 22A will be described in terms of use as a knee joint splint, so in this exemplary embodiment the proximal strut will be located along the thigh and the distal strut will be located on the leg below the knee. However, it will be understood that the invention is not limited to use with the knee joint, and splints for other body joints such as the elbow, ankle, and wrist can be similarly constructed using the principles described herein.

Pivot brackets 318 are mounted, for example by rivets, to the proximal strut 308, the proximal strut extension 311, and the distal strut 306 respectively.

In the preferred embodiment, the pivot brackets 318 and 322 are formed of sheet steel with a flat base 328. Two rounded pivot ears 330 extend at right angles, in parallel, from the flat base 328. Pivot holes 332 are provided in pivot ears 330 to receive a pin defining a pivot axis transverse to the length of the struts. Pins through holes 332 engage pivot assemblies 324 so that pivot assemblies 324 are attached to pivot brackets 318 and 322 and can be pivoted relative thereto about the pin axis. The extension of the pivot ears 330 may be varied depending on the position of the particular bracket along the splint, and also depending on which side of the limb the splint side 304 will support. The length of the pivot ears can be varied to adjust the position of the attached contour plates 334 with respect to the patient's limb. The pivot ear dimensions, which inherently establish the distances of the contour plates from the struts, may be established according to a typical anatomy, and fine adjustments in fit can be made by bending the struts or by varying the pad thickness.

Proximal strut extension 311 is attached to proximal strut 308. Proximal strut 308 has threaded holes 312 and proximal strut extension 311 has an elongated slot 314 which aligns with threaded holes 312. Fastening bolts 316 are installed through elongated slot 314 and into the threaded holes 312 to fix proximal strut extension 311 with respect to proximal strut 308. Significantly, the elongated slot 314 allows proximal strut extension 311 to take an infinite number of positions along the slot length relative to proximal strut 308. Thus, proximal strut extension 311 can be extended to any desired position within the length of elongated slot 314 prior to tightening of the fastening bolts 316.

Similarly, distal strut extension 320 is attached to distal strut 306. Because distal strut 306 has two pivot brackets mounted thereon, including one in the area of the distal strut extension 320 mounting point, it is convenient to integrate the connection of distal strut extension 320 and the connection of pivot bracket 322. Thus, pivot bracket 322 is preferably provided with threaded holes 326 in a bottom portion thereof, and distal strut 306 is provided with corresponding unthreaded holes aligned with holes 326. Fastening bolts 316 can then be installed through elongated slot 329 in distal strut extension 320, and then through the holes in the distal strut 306 and into threaded holes 326. Fastening bolts 316 are then tightened to hold together all three of the distal strut extension 320, distal strut 306, and pivot bracket 322. Elongated slot 329 allows distal strut extension 320 to take an infinite number of positions along the slot length relative to distal strut 306. Thus, distal strut extension 320 can be extended to any desired position within the length of elongated slot 329 prior to tightening of fastening bolts 316.

The positioning of the pivot brackets 318 and 322 is critical to ergonomically correct fitting of the splint. The pivot bracket 318 on the proximal strut 308 adjacent to the tension unit 310 is positioned close to the knee joint so that the pivot assemblies 324 attached thereto will rest firmly against the femoral condyle (bony prominence in the knee area). By virtue of the infinitely adjustable extension struts, the two pivot brackets 318 and attached pivot assemblies 324 that are located on the proximal strut extension 311 and the distal strut extension 320 respectively can be adjusted with reference to the physical dimensions of a particular patient so that the pivot assembly on the proximal strut extension 311 rests comfortably on the thigh and the pivot assembly on distal strut extension 320 locates above and against the malleoli (ankle bones). In this way, the splint is provided with superior bracing stability. The tendency of most splints of this type to migrate downward during movement is avoided by the positioning of the pivot assemblies on bony prominences of the limb.

Pivot assembly 324 comprises a metal contour plate 334, a pad 336, and strap retaining loops 338 on each side of the metal contour plate 334. Contour plates 334 are shaped to conform to the anatomical features in the area where the contour plates 334 will be installed. In the embodiment shown, contour plates 334 are generally shaped as a portion of a cylinder, with a linear cross section parallel to the length of the struts and an arcuate cross section along a given perpendicular to the length of the struts. Strap retaining loops 338 are steel loops with a linear portion around which straps (e.g. of the type shown in FIG. 28) can be installed. The pad 336 may be a piece of foam rubber or neoprene and preferably has unbroken loop material integrally affixed to the side facing the contour plate 334. Pads 336 may be selectively installed and removed from the contour plate 334 using a hook-and-loop fastening system. Preferably, different thicknesses of pads 336 may be. provided and selectively installed on the various contour plates to provide a custom fit based on the anatomical features of a specific patient.

FIG. 22B shows the pivot assembly 324 in more detail. Preferably, strap retaining loops 338 are pivotally mounted about an axis parallel to the length of the struts. A pivot bracket 340 is mounted on the underside of contour plate 334. The structure of pivot bracket 340 is similar to the structure of pivot brackets 318 and 322. Ears 344 fit between ears 330 of pivot brackets 318 and 322, so that upon installation of a pin or pins 342 through the holes 332 in pivot bracket 318 and corresponding holes in ears 344 aligned therewith, the pivot assembly 324 is pivotally connected to pivot bracket 318 or 322. Instead of a separate pivot bracket 340, the contour plate 334 can be provided with integral ears 344, for example cut and bent from the surface of contour plate 334, for engaging ears 330 of pivot bracket 318.

Preferably, a base portion of pivot bracket 340 is fastened to the contour plate 334, by rivets or other suitable fastening methods. Hook fastener material 346 for mating with the loop material on pad 336 is attached to the top surface of contour plate 334 by an acrylic adhesive. It has been found that the hook fastener material 346 tends to creep along the smooth surface of the contour plate 334, particularly in warm weather and if rubber-based adhesives are used. To further eliminate this problem, it has also been found desirable to rivet pivot bracket 340 to the contour plate 334 after installation of hook fastener material 346 so that the rivets pass through hook fastener material 346, holding it in place.

Figure 23A:
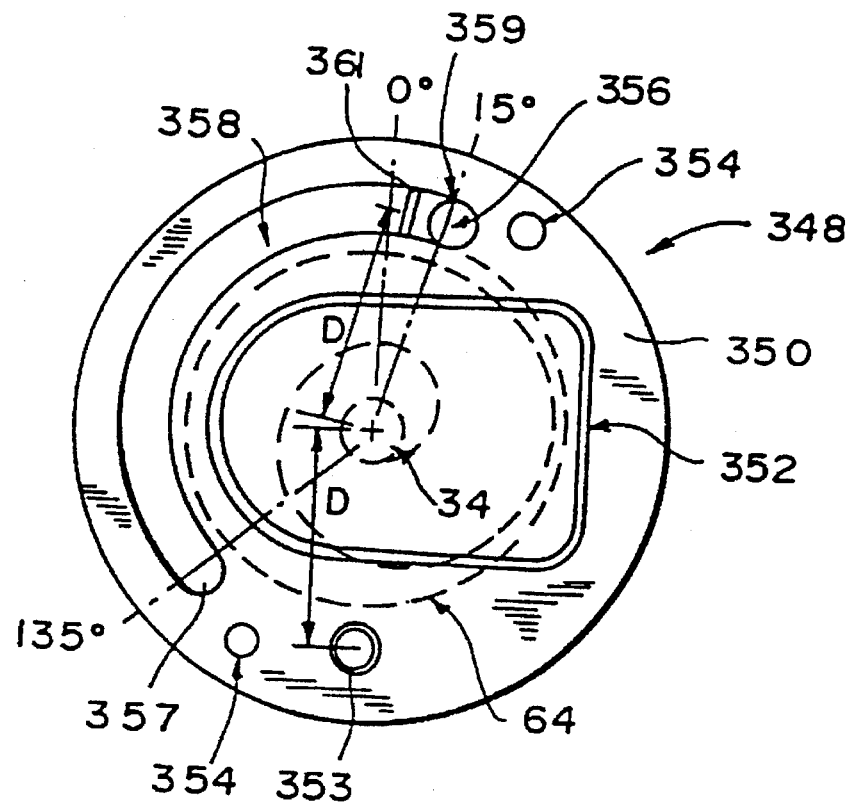
FIG. 23A is a top view of the bi-directional dynamic tension unit according to the present invention.

FIG. 23A shows a bi-directional dynamic tension unit according to the present invention. Dynamic tension unit 348 comprises a housing 350 enclosing a circular leaf spring 64 which is connected to pivot post 34. There is also provided an adjustment mechanism 352 of a type described above, e.g. with reference to FIG. 3, comprising an adjusting gear that can be rotated to turn the pivot pin and thereby change the tension in circular leaf spring 64. Housing 350 is held together by a plurality of connecting pins 354. A hole 353 in the housing 350 provides a fixed mounting position whereby one of the splint struts can be selectively locked to the dynamic tension unit 348.

The outside end of the circular leaf spring 64 terminates in a loop 356 disposed for arcuate movement in an arcuate slot 358 in the housing. For knee use, the arcuate slot 358 preferably extends through 150 degrees of arc. Specifically, establishing zero degrees as the intersection of the line connecting the centers of hole 353 and pivot post 34 with the arcuate slot 358, and looking down at the top of housing 350, the arcuate slot 358 extends for 150 degrees of arc, between +15 degrees of arc at end 359 and −135 degrees of arc at end 357.

Loop 356 can be pulled away from end 359 of slot 358 and a stop 361 installed in slot 358 of dynamic tension unit 348, to confine the extension range to the area of slot 358 between −135° and 0°. The full range extending to +15° is only used after sufficient healing has taken place. Then, maximum extension is achievable by permitting this 15° of hyperextension.

Significantly, the radial distance D from the central axis of pivot post 34 to the center of hole 353 is made equal to the radial distance D from the center of pivot post 34 to the center of loop 356. Typically, D may be equal to about 1.25 inches, but D can be larger or smaller depending on the size of the dynamic tension unit 348 and the application (e.g. wrist, elbow, leg, etc.). As will be seen, making these distances equal facilitates disconnecting the dynamic tension unit 348 from the struts and reversing its connection to the struts, thereby reversing the force application to the limb.

Loop 356 at the end of spring 64 is a floating mounting point to which the strut other than the strut connected to hole 353 is fixed, in a manner which will be explained in more detail below.

Figure 23B:
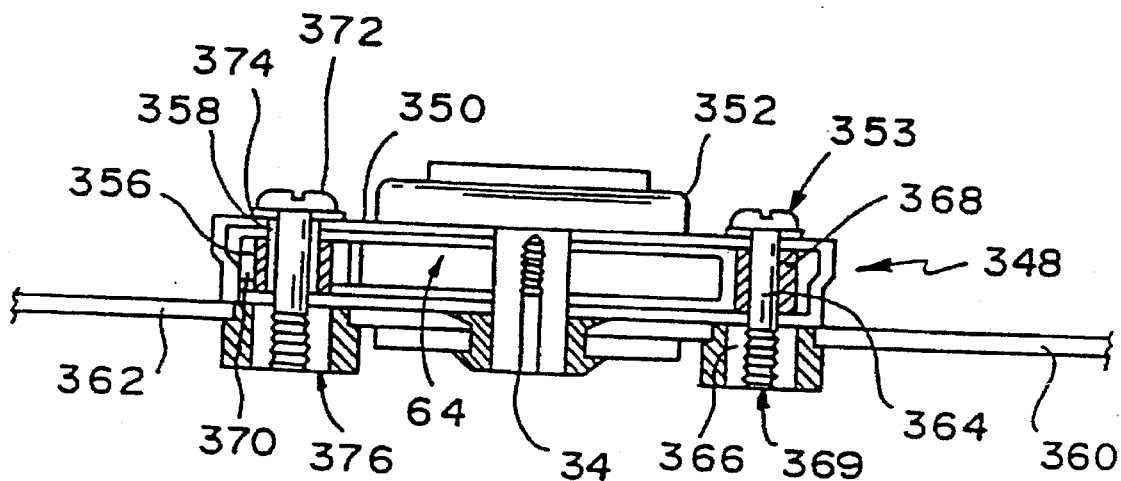
FIG. 23B is a cross-sectional view showing the assembly of the bi-directional dynamic tension unit of FIG. 23A.

The internal construction of the bi-directional tension unit of FIG. 23A is shown in greater detail in the cross-sectional view of FIG. 23B, which is taken along the line extending between the centers of hole 353 and pivot post 34. As can be seen, struts 360 and 362 are rotatably connected about pivot post 34.

Strut 360 is attached to housing 350 in the following manner. As shown in FIG. 23B, the housing walls about hole 353 of housing 350 are structurally reinforced by a tubular member 368. Strut 360 has a hole 366, and a machine screw 364 is installed through a washer, into hole 353 of housing 350 and into the hole 366. Hole 366 may be provided with a threaded insert or nut 369 to receive machine screw 364 as shown, so that when machine screw 364 is installed it can be tightened to rigidly fix strut 360 relative to housing 350. Of course, the machine screw arrangement shown is only one way of preventing relative movement of strut 360 relative to housing 350. Various other fastening means could also be used, for example locking pins, cotter pins, clamps, or various nut-and-bolt combinations.

The floating mounting point of spring 64, that is loop 356, is used to attach shut 362 to the spring 64. With this attachment, shut 362 is rotatable relative to housing 350 and strut 360 about pivot post 34. Spring 64 will apply a force aiding rotation of shut 362 in one direction and opposing rotation in the opposite direction. The force applied by spring 64 will always tend to move the rotating shut in the direction of end 359 of slot 358. As shown in FIG. 23B, a sleeve 370 is provided in the loop 356 of spring 64 and is rotatable relative to loop 356. A shoulder bolt 372 is installed through a teflon or nylon washer 374, through sleeve 370, and into a threaded insert 376 installed in shut 362, thus fixing shut 362 to loop 356 of spring 64. As with shut 360 above, the bolt 372 may thread into an insert in shut 362 so as to fix loop 356 to shut 362.

In the preferred embodiment, circular leaf spring 64 is attached to pivot post 34, and a tension adjustment of the type described above with reference to FIG. 3 is provided to linearly vary the tension in circular leaf spring 64. However, those skilled in the art will appreciate that various other types of springs could also be used to implement the reversible tension unit of the present invention. For example, a long coil-type spring or even an elastomeric band (not shown) could be connected to loop 356, disposed clockwise around the inside periphery of housing 350, and attached to the housing 350 at an attachment point (not shown) adjacent to end 357 of slot 358. As can be appreciated, while it is convenient and desirable to attach circular leaf spring 64 to the pivot post 34 to facilitate a linear force adjustment feature, spring 64 or a spring of a different configuration could also be attached to other points in or about housing 350. What is important is that one end of the spring or other force application means be attached to the loop 356, and the other to a point that can be fixed relative to the housing 350. As noted above, the actual point of attachment may desirably be movable with respect to the housing 350 for adjustment of tension, but the point of attachment may be held immobile with respect to housing 350 during use of the splint.

As will be seen, with properly configured struts it is possible to attach housing 350 to either of the struts through hole 353, and attach loop 356 to the other strut. Depending on which strut is attached to which part of the dynamic tension unit 348, the dynamic tension unit 348 will operate in either a flexion or contraction mode. That is, the dynamic tension unit 348 can apply force in either direction depending on the attachment to the struts.

Figure 24:
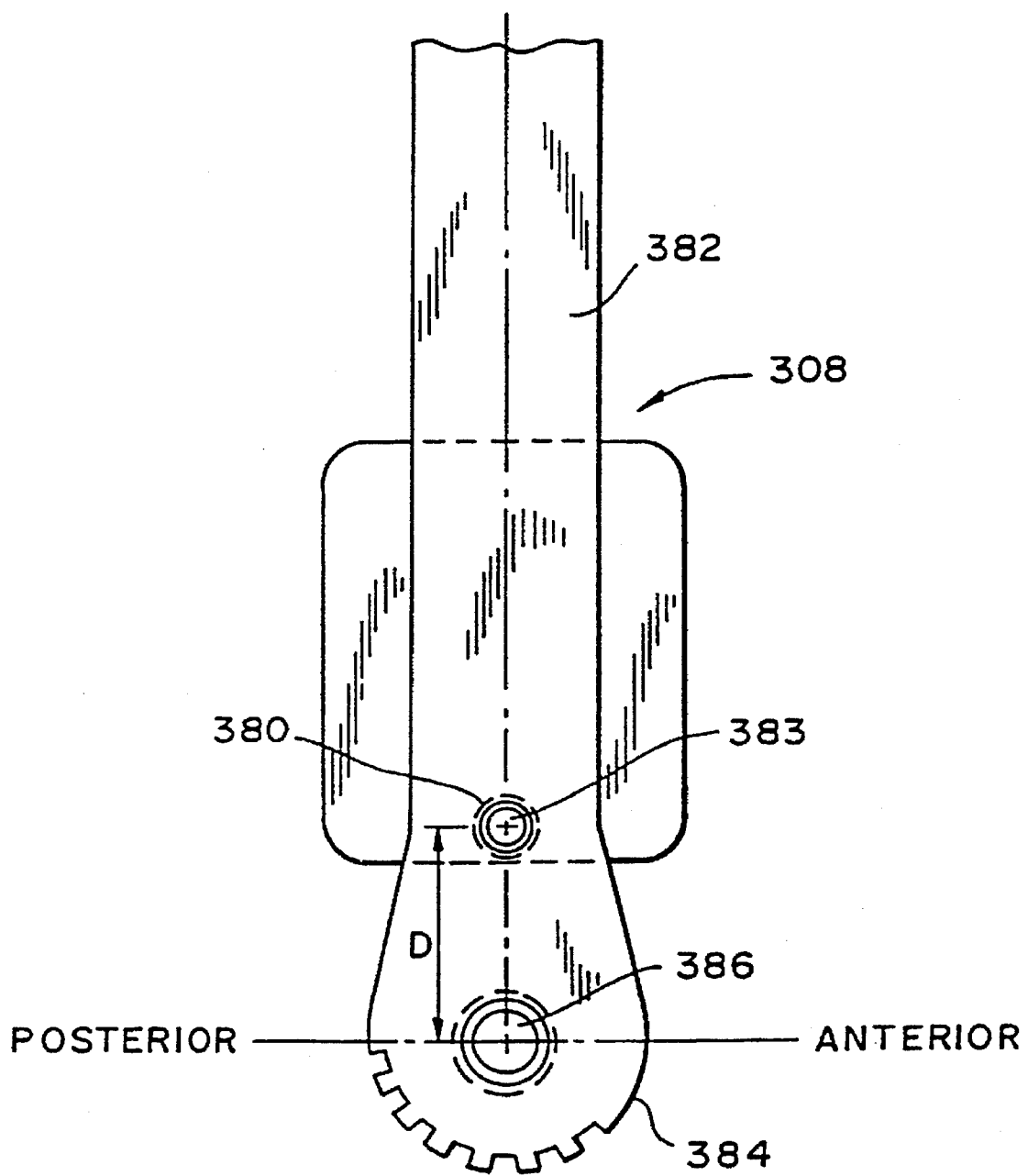
FIG. 24 is a plan view of a proximal strut of the bidirectional dynamic splint of the present invention.
Figure 25:
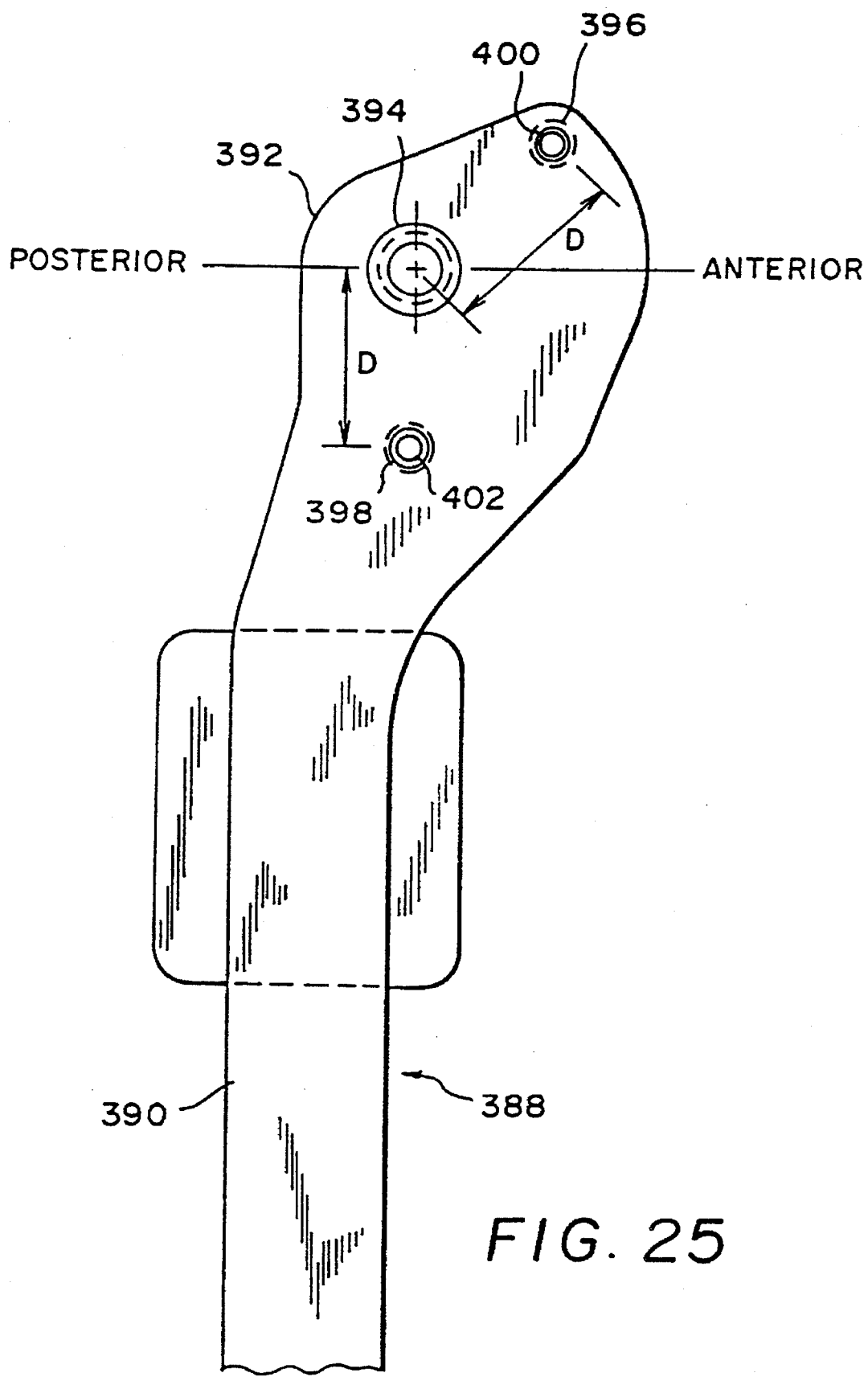
FIG. 25 is a plan view of a distal strut of the bidirectional dynamic splint of the present invention.

The effective bi-directional operation and easy reversibility of dynamic tension unit 348 provided by the present invention requires that the struts be specially adapted to facilitate reversible operation. FIGS. 24 and 25 illustrate the construction of proximal and distal struts, respectively, which facilitate reversible operation of dynamic tension unit 348 in a leg splint.

Referring now to FIG. 24, there is shown a proximal strut 308 used with the bi-directional dynamic splint of the present invention. Proximal strut 308 comprises an elongated strut portion 382 and a pivot portion 384. Pivot portion 384 has a centrally located hole 386 which engages pivot post 34 (shown in FIG. 23B). A mounting hole 380 is spaced at a distance D from hole 386 (equal to the distance D indicated in FIG. 23A) in a direction along the length of proximal strut 308. Mounting hole 380 has a threaded insert 383 for receiving a threaded fastener. Preferably, pivot portion 384 may also be provided with detents for use with locking mechanisms, of the type illustrated in either FIG. 20 or 21.

Referring now to FIG. 25, a distal strut 388 designed to facilitate reversible splint operation has an elongated strut portion 390 and a pivot portion 392. Pivot portion 392 has a centrally located hole 394 for receiving pivot post 34. Pivot portion 392 also has two holes 396 and 398, each spaced at distance D from the center of hole 394. Hole 398 is located distance D along a line generally parallel to the length of elongated strut portion 390. Hole 396 is located a distance D along a line at about a 45° angle to the length of elongated strut portion 390. Note that the centerline of elongated strut portion 390 is offset from the pivot which is in line with the proximal strut 382. Typical human anatomy dictates a ⅝" offset. However, the design shown can be readily adapted to provide any desired offset.

Holes 396 and 398 are each provided with a threaded insert 400 and 402 respectively for receiving a threaded fastener. As will be seen, hole 396 is attached to the floating mount of spring loop 356 when flexion mode operation is desired, and hole 396 is not used in extension mode operation. Hole 398 is fixed to hole 353 when extension mode operation is desired, but is not used in flexion mode. Thus, in the case of distal strut 388, different mounting holes are selectively used to achieve different operational modes. As will be seen, the use of different mounting holes facilitates reversible operation using the same dynamic tension unit 348. The use of different mounting holes repositions the distal strut so that the desired rage of motion of the strut under tension corresponds to the rage of motion provided by the slot 358 of dynamic tension unit 348, in either the flexion or extension modes respectively.

FIG. 26A shows the bi-directional power unit connected for flexion operation. Proximal strut 308 and distal strut 388 are connected to rotate about pivot post 34 of reversible dynamic tension unit 348. Preferably, as described above with reference to FIG. 21, struts 308 and 388 are joined by a hollow pivot affixing them rotatably, relative to each other. Pivot post 34 of dynamic tension unit 348 extends into this hollow pivot to fixedly locate the pivot axis relative to dynamic tension unit 348. As will be seen, screws attaching different parts of struts 308 and 388 to the dynamic tension unit 348 will effectively hold the hollow pivot in place without further attachment of the hollow pivot at pivot post 34. By providing a slip fit between pivot post 34 and the hollow pivot connecting the struts, the dynamic tension unit 348 can be easily removed from and installed on the strut assembly of the type shown in FIG. 21. In this way, the strut assembly and associated contour plates and cuff/strap parts can be used as a non-tensioned brace. The dynamic tension unit 348 or "power unit" can then be installed, if desired to convert the brace into a dynamic tension flexion/extension splint.

However, a snap ring, cotter pin, or other mechanism which locks the struts in place for rotation about pivot post 34, yet permits disassembly of the mechanism using appropriate tools, could also be provided if desired.

To make the attachments for flexion operation, a machine screw placed in hole 353 or other pin arrangement of dynamic tension unit 348 is attached to threaded insert 383 of hole 380 of proximal strut 308. Similarly, a machine screw placed through spring loop 356 is attached to threaded insert 400 of hole 396 in distal strut 388. Thus, the body of dynamic tension unit 348 is fixed to proximal strut 308 and the end of the spring 64 is connected to the distal strut. With these connections, the force of spring 64 urges the connection of the distal strut at hole 396 toward end 359 of the slot 358. Thus, the distal strut will tend to rotate clockwise in the view shown with respect to the proximal strut.

Figure 26B:
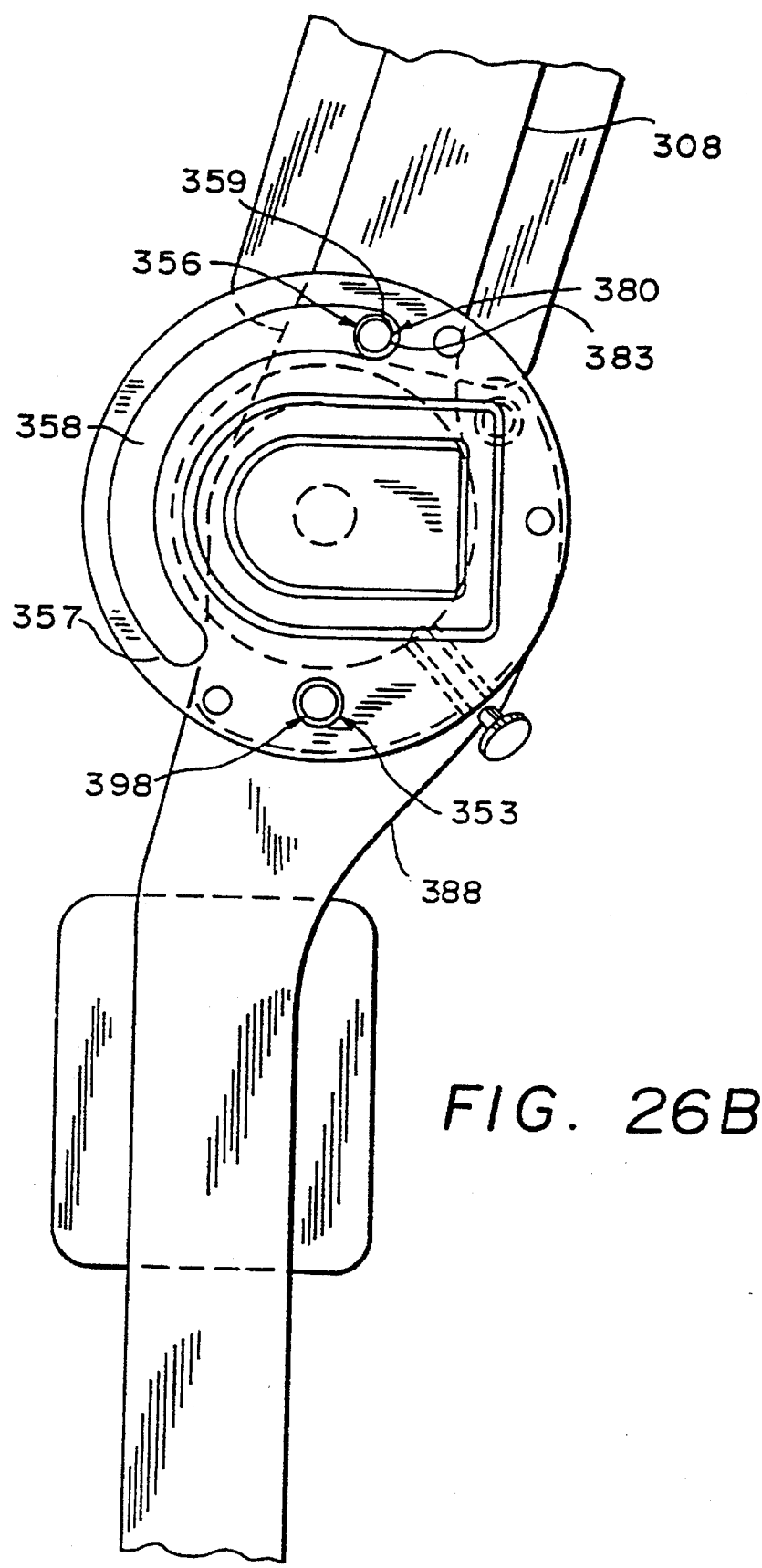
FIG. 26B shows the bi-directional power unit connected in position for extension operation.

FIG. 26B shows the bi-directional dynamic tension unit 348 locked in position for extension operation. To change the mode of operation of the unit from the flexion mode of FIG. 26A to the extension mode of FIG. 26B, the connections of the struts to the body of dynamic extension unit 348 and the spring 64, as specified above with reference to FIG. 26A, are removed. The dynamic tension unit 348 is then rotated, with respect to the struts, about pivot post 34, and the distal strut is rotated as necessary, to create a new alignment of attachment points appropriate for the extension mode. Referring now to FIG. 26B, for the extension mode, the fixed mounting hole 353 is connected to the distal strut by installing a machine bolt or other appropriate fastener through hole 353 into threaded insert 402 in hole 398 of the distal strut 388. The floating point mounting, at spring loop 356, is connected to the proximal strut by installing a machine bolt or other appropriate fastener through spring loop 356 into threaded insert 383 of hole 380 of the proximal strut. In this way, the direction of the force applied by dynamic tension unit 348 is reversed.

In each of the two modes, one of the two attachment points (356, 353) on the dynamic tension unit 348 is always connected to hole 380 of the proximal strut. In contrast, a different hole on the distal strut is used in each mode. The use of different mounting holes on the distal strut repositions the distal strut so that the desired range of motion of the strut under tension corresponds to the range of motion provided by the slot 358 of dynamic tension unit 348. Thus, the positioning of the holes in the distal strut is relatively critical in assuring that the desired range of motion (and limits on the range of motion) will be obtained in each mode.

It will be understood that in the description above of the bi-directional reversible dynamic tension unit 348, only one set of struts and the corresponding dynamic tension unit has been described. Those skilled in the art will appreciate that a complete splint according to the present invention is formed using the structure shown and described on one side of an affected limb, and also using a mirror-image structure on the opposite side of the limb. The two sides of the splint are attached using strap means to hold each side in place against the limb.

Figure 27A:
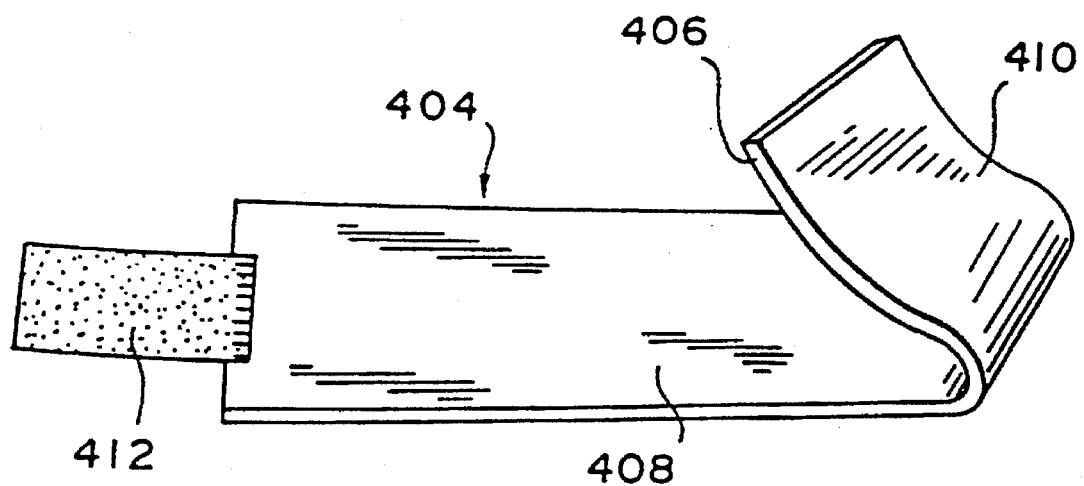
FIG. 27A shows an improved single cuff/strap assembly according to the present invention.

A preferred method of assembling and attaching the completed splint will be described with reference to FIG. 27. FIG. 27A shows an improved single soft cuff/strap assembly according to the present invention. Cuff/strap assembly 404 comprises neoprene foam strip 406, typically about 2.5 inches wide and 15 to 25 inches long. Cuff/strap assembly 404 is covered entirely by different fabric layers on its two sides: on one side by a low stretch nylon cover 408 and on the other side by an unbroken loop material 410. A 1.5 inch by three inch length of double-sided hook material 412 for engaging the unbroken loop material 410 is sewn onto the assembly by a double row of heavy stitching, and extends from the end of cuff/strap assembly 404 as shown. The hook material 412 may be of the type known as Velcro (TM) and has hook fasteners on both sides for engaging unbroken loop material 410. The hook material can be provided with hooks on both sides or single-sided hook material can be glued together to provide a structure with hooks covering both sides.

Figure 27B:
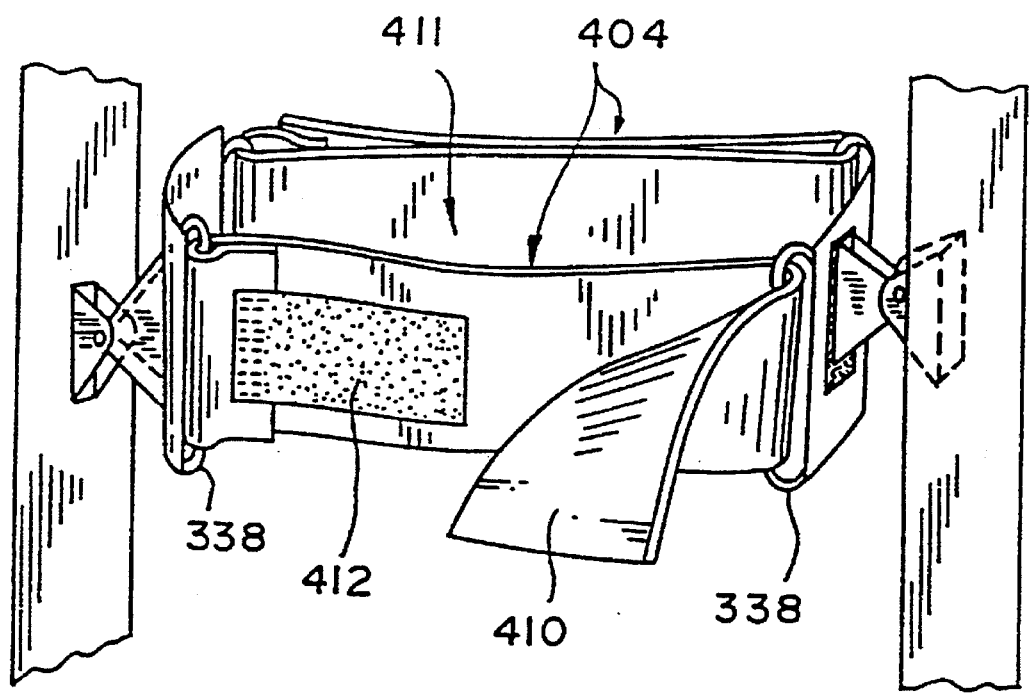
FIG. 27B shows the assembly of FIG. 27A installed on the adjustable dynamic splint of FIG. 22.

FIG. 27B shows the assembly of FIG. 27A installed on the adjustable dynamic splint of FIG. 22. The hook end of cuff/strap assembly 404 is passed through retaining loop 338 and doubled back with the unbroken loop side facing the retaining loop. The hook material is pressed into engagement with the unbroken loops to seal the cuff/strap assembly 404 about the retaining loop 338. The other end of cuff/strap assembly 404 is passed through retaining loop 338 of the strut on the opposite side of the limb. The limb is omitted from the drawing for clarity but is located in limb area 411, between the struts and also between the front and back cuff/strap assemblies 404. Cuff/strap assembly is then pulled to the desired tightness and the surface of unbroken loop material 410 is engaged with the surface of exposed hook material 412. In this way, cuff/strap assembly 404 is locked together to hold the struts in position against the limb. This strap arrangement provides universal length adjustment and can be trimmed easily for a custom fit. The installation of the cuff/strap assembly with a double thickness at any given point adjacent to the limb provides increased comfort and resistance to lengthwise stretching.

The use of neoprene foam in cuff/strap assembly 404 maintains a desirable cushioning effect to increase patient comfort, and the layer of low stretch nylon reduces stretching of the cuff/strap assembly which could result in instability of the splint installation. The doubling over of cuff/strap assembly 404 when installed as shown in FIG. 28B also tends to reduce stretching of the cuff/strap assembly 404. A designed balance is necessary in the amount of stretch of cuff/strap assembly 404. It is desirable to permit some stretching to compensate for muscle bulge when the underlying muscles are tensed during use. However, the amount of stretching should at the same time be design-limited so that the splint does not loosen during use and thus fail to provide the desired support.

The number and location of cuff/strap assemblies 404 will vary depending on the structure of the splint and the joint to which the device will be applied (e.g. elbow, wrist, knee, ankle, etc.). In general, for a knee splint of the type shown in FIG. 22A, ten cuff/strap assemblies 404 will be provided: that is, both a front and a back cuff/strap assembly 404 will be provided at each of the five pivot assemblies 324.

Industrial Applicability

The dynamic splint of the present invention is used for the treatment of joint contractures occurring secondary to trauma, casting, or other immobilization. It is also used to restore strength and flexibility to a body joint, by creating resistance requiring the wearer to flex the joint, thereby building strength and fluidity. The bias adjustment feature incorporated within the dynamic extension splint permits the spring bias of the splint to be varied throughout a recovery process as treatment of the joint progresses.

The dynamic splints disclosed permit maintenance of a defined tolerable force level with maximum linearity over a wide range of motion of a body joint. The dynamic splints are particularly useful for prophylactic maintenance of range-of-motion and mobility, particular in post-operative cases.

We claim:

1. An adjustable splint device for applying force across a body joint comprising:

a first strut member, a second strut member, a joint assembly including a support separate from said first and second strut members, pivot means mounted on said support for mounting said first and second strut members, said pivot means mounting at least one of said strut members for relative pivotal movement to the remaining strut member about a pivot axis, and a bias unit connected to said joint assembly and connectable to one of said strut members for applying a bias force opposing relative pivotal movement between said first and second strut members in a first of two opposite directions and aiding such pivotal movement in a second of said opposite directions, said support being rotatable separately from said first and second strut members relative to said pivot axis between a first flexion mode position and a second extension mode position, and mode reversing connection means to cause said bias unit to apply said bias force to said first or second strut members in either a flexion mode or an extension mode, said mode reversing connection means operating in said flexion mode to connect said support to said first strut member and to connect said bias unit to said second strut member so that said bias unit biases pivotal movement of said second strut member relative to said first strut member in a first direction and operating in an extension mode to connect said support to said second strut member and to connect said bias unit to said first strut member so that said bias unit biases pivotal movement of said first strut member relative to said second strut member in a second direction opposite to said first direction.

2. The adjustable splint device of claim 1 wherein both said first and second strut members are mounted for pivotal movement on said pivot means, said mode reversing connection means operating to prevent pivotal movement of said first strut member about said pivot means relative to said support in said flexion mode and to prevent pivotal movement of said second strut member about said pivot means relative to said support in the extension mode.

3. The adjustable splint device of claim 2 wherein said mode reversing connection means leaves said second strut member free for pivotal movement about said pivot means in said flexion mode and leaves said first strut member free for pivotal movement about said pivot means in said extension mode.

4. The adjustable splint device of claim 3 which includes bias adjustment means mounted on said support and connected to said bias unit for adjusting a magnitude of bias force applied by said bias unit.

5. The adjustable splint device of claim 3 wherein said bias unit includes a spring having a first end connected to said support and a second end connectable to said second strut member in the flexion mode and to said first strut member in the extension mode, said support including an arcuate guide equally spaced from said pivot means along its length, the second end of said spring being retained for movement in said arcuate guide.

6. The adjustable splint device of claim 5 which includes bias adjustment means mounted on said support and connected to the first end of said spring for adjusting the magnitude of bias force applied by said bias unit.

7. The adjustable splint device of claim 5 wherein said arcuate guide includes a first end and a second end, said support being positioned relative to said first and second strut members in said flexion mode by said mode reversing connection means to position said second end of said spring for connection to bias said second strut member toward the first end of said arcuate guide and in the extension mode to position the second end of said spring for connection to bias said first strut member toward the second end of said arcuate guide.

8. The adjustable splint device of claim 7 wherein said first and second strut members each include a first end, a pivot connection formed in the first ends of said first and second strut members to mount said first and second strut members on said pivot means, said mode reversing connection means including a spring connector formed at the second end of said spring and first fastening means spaced from the pivot connection at the first ends of said first and second strut members, said first fastening means on said first strut member operating to connect said first strut member to said support in the flexion mode and to connect said first strut member to said spring connector in the extension mode, said first fastening means on said second strut member operating to connect said second strut member to said spring connector in the flexion mode.

9. The adjustable splint device of claim 8 herein said second strut member includes second fastening means spaced from the first fastening means and the pivot connection on said second strut member, said second fastening means operating to connect said second strut member to said support in the extension mode.

10. The adjustable splint device of claim 9 wherein the first fastening means on the first and second strut members and the second fastening means on the second strut member are spaced from said pivot connection by a distance equal to the distance said pivot means is spaced from said arcuate guide.

11. The adjustable splint device of claim 10 wherein said second strut member includes a central longitudinal axis, said pivot connection and first fastening means of said second strut member being aligned along a line parallel with the central longitudinal axis of said second strut member and said second fastening means being radially positioned relative to said second strut member pivot connection along a radial line at an angle to said central longitudinal axis.

12. The adjustable splint device of claim 11 wherein said second strut member second fastening means is positioned along a radial line extending at an angle of 45 degrees to said central longitudinal axis.

13. The device of claim 2 further comprising cam locking means for selectively engaging an element connected to said first strut and an element connected to said second strut by cam action to prevent relative movement of said first and second struts.

14. The adjustable splint device of claim 1 wherein said bias unit includes a spring having a first end connected to said support and a second end connectable to said second strut member in the flexion mode and to said first strut member in the extension mode, said support including an arcuate guide equally spaced from said pivot means along its length, the second end of said spring being retained for movement in said arcuate guide.

15. The adjustable splint device of claim 14 wherein said arcuate guide includes a first end and a second end, said support being positioned relative to said first and second strut members in said flexion mode by said mode reversing means to position said second end of said spring for connection to bias said second strut member toward the first end of said arcuate guide and in the extension mode to position the second end of said spring for connection to bias said first strut member toward the second end of said arcuate guide.

16. The adjustable splint device of claim 15 which includes bias adjustment means mounted on said support and connected to the first end of said spring for adjusting the magnitude of bias force applied by said bias unit.

17. The adjustable splint of claim 1 which includes locking means for selectively locking said first and second strut members against relative pivotal movement, said locking means including detents formed on one of said strut members and a detent engaging lock mounted on the remaining strut member to engage said detents.

18. An adjustable splint device for applying force across a body joint comprising a first strut member, a second strut member, at least one of said first and second strut members having a pivoted limb engaging cuff assembly mounted thereon, said cuff assembly including an arcuate contour plate and a plate mount assembly secured to said strut member and to said contour plate, said plate mount assembly including a plate pivot transverse to the longitudinal axis of said strut member for mounting said contour plate for pivotal movement about said plate pivot and strap retaining means formed on said contour plate and pivotal therewith, a joint assembly for connecting the first strut member to the second strut member for relative pivotal movement about a pivot axis, said joint assembly including a pivot for mounting at least one of said first and second strut members for pivotal movement about said pivot, and a bias unit connected to provide a bias to oppose pivotal movement of said first and second strut members in a first direction and to aid such pivotal to said first direction opposite to said first direction, said bias unit being connected to at least one of said first and second strut members.

19. The adjustable splint device of claim 18 wherein said contour plate includes a concave surface facing outwardly away from the surface of the strut member upon which said limb engaging cuff assembly is mounted, said strap retaining means including strap retaining loops secured to said arcuate contour plate and extending along opposite sides thereof substantially parallel to the longitudinal axis of said strut member.

20. An adjustable splint device for applying force across a body joint comprising:

a first strut member, a second strut member, said first and second strut members being mounted for relative pivotal movement, a joint assembly including a support housing, separate from said first and second strut members, a pivot connected to said support housing for mounting said support housing for rotation relative to said first and second strut members, and a bias unit connected to said joint assembly and to one of said strut members for applying a bias force opposing relative pivotal movement between said first and second strut members in a first of two opposite directions and aiding such pivotal movement in a second of said opposite directions, said bias unit including a spring mounted in said support housing, the support housing being rotatable relative to said first and second strut members between a flexion position and an extension position to cause said bias unit to apply said bias force to said first or second strut members in either a flexion mode or an extension mode, and connection means operating in said flexion mode to connect said support housing to said first strut member and said bias means to said second strut member so that said bias means biases pivotal movement of said second strut member relative to said first strut member in a first direction and operating in an extension mode to connect said support housing to said second strut member and said bias means to said first strut member so that said bias means biases pivotal movement of said first strut member relative to said second strut member in a second direction opposite to said first direction.

21. The adjustable splint device of claim 20 wherein both said first and second strut members are mounted for pivotal movement about said pivot.

22. The adjustable splint device of claim 21 wherein said bias unit includes a spring having a first end connected to said adjustment means and a second end connectable by said connection means to said second strut member in the flexion mode and to said first strut member in the extension mode, said support housing including an arcuate guide equally spaced from said pivot along its length, the second end of said spring being retained for movement in said arcuate guide.

23. The adjustable splint device of claim 22 wherein said arcuate guide includes a first end and a second end, said support housing being positioned relative to said first and second strut members in said flexion position to position said second end of said spring for connection to bias said second strut member toward the first end of said arcuate guide and in the extension position to position the second end of said spring for connection to bias said first strut member toward the second end of said arcuate guide.

24. The adjustable splint device of claim 20 which includes bias adjustment means mounted on said support housing and connected to said bias unit for adjusting a magnitude of bias force applied by said bias unit, said adjustment means rotating with said support housing between the flexion and extension positions to maintain the adjusted magnitude of bias force in both the flexion and extension modes.

25. A bias unit for connection to an adjustable splint which includes first and second strut members mounted for pivotal movement around a pivot comprising a housing, a post mounted for rotation on said housing, an arcuate guide formed in said housing and spaced radially from said post, and an elongate leaf spring mounted within said housing and wrapped around said post, said leaf spring having a first end connected to said post and a second end mounted for movement in said arcuate guide.

26. The bias unit of claim 25 wherein the second end of said leaf spring is retained in said arcuate guide.

27. The bias unit of claim 26 wherein said arcuate guide is an arcuate slot formed in said housing.

28. The bias unit of claim 27 which includes bias adjustment means mounted on said housing and operative to rotate said post to adjust the bias of said spring.

29. The bias unit of claim 28 wherein said bias adjustment means includes a gear secured to said post, and a rotatable shaft mounted on said housing to engage and rotate said gear.

30. The bias unit of claim 28 wherein a bias indicator is secured to said post to rotate therewith and spaced indicia are provided upon said bias indicator to indicate the degree of bias provided by said spring.

31. The bias unit of claim 30 which includes first mounting means for removably securing said housing to one of said first and second struts and second mounting means for removably securing the second end of said spring to said remaining strut.

32. The bias unit of claim 31 wherein the second end of said spring is provided with bolt receiving means to receive a bolt, said second mounting means including a bolt which projects through said arcuate slot and the bolt receiving means to one of said first and second struts.

33. The bias unit of claim 25 which includes first mounting means for securing said housing to said first strut member and second mounting means for securing the second end of said spring to said second strut member.

34. The bias unit of claim 33 wherein said first mounting means removably secures said housing to said first strut member and said second mounting means removably secures said second end of said spring to said second strut member to facilitate removal of said housing from said first and second strut members.

* * * * *